(12) United States Patent
Bitran et al.

(10) Patent No.: US 10,678,890 B2
(45) Date of Patent: Jun. 9, 2020

(54) CLIENT COMPUTING DEVICE HEALTH-RELATED SUGGESTIONS

(71) Applicant: Microsoft Technology Licensing, LLC, Redmond, WA (US)

(72) Inventors: Hadas Bitran, Ramat Hasharon (IL); Todd Holmdahl, Redmond, WA (US); Eric Horvitz, Kirkland, WA (US); Desney S. Tan, Kirkland, WA (US); Dennis Paul Schmuland, Redmond, WA (US); Adam T. Berns, Issaquah, WA (US); Brian Bilodeau, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 672 days.

(21) Appl. No.: 14/971,702

(22) Filed: Dec. 16, 2015

(65) Prior Publication Data

US 2017/0039327 A1 Feb. 9, 2017

Related U.S. Application Data

(60) Provisional application No. 62/202,119, filed on Aug. 6, 2015.

(51) Int. Cl.
*H04L 29/06* (2006.01)
*G06F 19/00* (2018.01)
(Continued)

(52) U.S. Cl.
CPC ........... *G06F 19/324* (2013.01); *G16H 20/30* (2018.01); *G16H 20/60* (2018.01); *G16H 20/70* (2018.01);
(Continued)

(58) Field of Classification Search
None
See application file for complete search history.

(56) References Cited

U.S. PATENT DOCUMENTS 7,447,643 B1 11/2008 Olson et al.
8,073,708 B1 * 12/2011 Igoe ...................... G06Q 40/00
705/2

(Continued)

FOREIGN PATENT DOCUMENTS

WO 2012006669 A1 1/2012

OTHER PUBLICATIONS

ISA European Patent Office, International Search Report and Written Opinion Issued in PCT Application No. PCT/US2016/043225, dated Sep. 12, 2016, WIPO, 9 pages.

(Continued)

*Primary Examiner* — Michael Tomaszewski
(74) *Attorney, Agent, or Firm* — Alleman Hall Creasman & Tuttle LLP

(57) ABSTRACT

A client computing device is disclosed that comprises a processor and an electronic personal assistant application program. The personal assistant application program may be configured to capture user data associated with user activities across a plurality of computer programs. The user data may be sent to a personal assistant user data interpretation engine. A health-related suggestion based on at least a subset of the user data and anonymized statistics of a user population retrieved from an aggregated knowledge base may be received. The health-related suggestion may be displayed on a display associated with the client computing device.

19 Claims, 18 Drawing Sheets

(51) Int. Cl.
*H04L 29/08* (2006.01)
*G16H 50/70* (2018.01)
*G16H 50/20* (2018.01)
*G16H 20/60* (2018.01)
*G16H 20/30* (2018.01)
*G16H 70/20* (2018.01)
*G16H 40/63* (2018.01)
*G16H 20/70* (2018.01)

(52) U.S. Cl.
CPC .............. *G16H 40/63* (2018.01); *G16H 50/20* (2018.01); *G16H 50/70* (2018.01); *G16H 70/20* (2018.01); *H04L 63/0421* (2013.01); *H04L 67/02* (2013.01)

(56) References Cited

U.S. PATENT DOCUMENTS

| | | | |
|---|---|---|---|
| 8,358,214 | B2 | 1/2013 | Amigo et al. |
| 8,781,849 | B1* | 7/2014 | Grossman .............. G06Q 50/24 705/2 |
| 2009/0198733 | A1 | 8/2009 | Gounares et al. |
| 2011/0213332 | A1* | 9/2011 | Mozayeny .......... A61M 5/1723 604/503 |
| 2012/0005030 | A1 | 1/2012 | Valin et al. |
| 2012/0016690 | A1* | 1/2012 | Ramarajan ............. G06Q 50/22 705/2 |
| 2012/0179665 | A1 | 7/2012 | Baarman et al. |
| 2013/0268292 | A1 | 10/2013 | Kim et al. |
| 2014/0088996 | A1 | 3/2014 | Damani |
| 2014/0121540 | A1 | 5/2014 | Raskin |
| 2014/0121564 | A1 | 5/2014 | Raskin |
| 2014/0129240 | A1* | 5/2014 | Zhang ................... G06Q 50/22 705/2 |
| 2014/0244292 | A1* | 8/2014 | Rosenberg ............ G06F 19/324 705/2 |
| 2014/0247146 | A1 | 9/2014 | Proud |
| 2014/0289220 | A1 | 9/2014 | Gottfurcht et al. |
| 2015/0112158 | A1 | 4/2015 | He et al. |
| 2015/0164435 | A1 | 6/2015 | Nagarajan |
| 2015/0196256 | A1 | 7/2015 | Venkatraman et al. |
| 2015/0356701 | A1* | 12/2015 | Gandy ................... G06Q 50/22 705/2 |

OTHER PUBLICATIONS

Valverde, et al., "Heart Health Risk Assessment System: A Nonintrusive Proposal Using Ontologies and Expert Rules", In Journal of BioMed Research International vol. 2014, Jun. 15, 2014, pp. 1-13.

Hritzuk, et al., "Consumer Decision Journey: Health and Wellness", Retrieved on: Aug. 17, 2015 Available at: http://advertising.microsoft.com/en/cl/6933/consumer-decision-journey-health-and-wellness.

Tozzi, et al., "Bloomberg: Your Google searches could help the FDA find drug side-effects", Published on: Jul. 15, 2015 Available at; http://www.bloomberg.com/news/articles/2015-07-15/your-google-searches-could-help-the-fda-find-drug-side-effects.

Buytendijk, F. et al., "Summary and Link to Purchase 'Analytics Gets Personal with the Quantified Self'," Gartner, Inc. Website, Available Online at https://www.gartner.com/doc/2487617?ref=ddisp, May 17, 2013, 2 pages.

McIntyre, A. et al., "Summary and Link to Purchase 'Market Trends: Enter the Wearable Electronics Market With Products for the Quantified Self'," Gartner, Inc. Website, Available Online at https://www.gartner.com/doc/2537715?ref=ddisp, Jul. 1, 2013, 2 pages.

Gotta, S., "Summary and Link to Purchase 'Technology Overview: Quantified Self'," Gartner, Inc. Website, Available Online at https://www.gartner.com/doc/2591327?ref=ddisp, Sep. 17, 2013, 2 pages.

Dunbrack, L., "Abstract and Link to Purchase 'Perspective: The Consumer Experience—Why Consumers Stop Using Fitness Trackers'," IDC Research, Inc. Website, Available Online at http://www.idc.com/getdoc.jsp?containerId=HI249613, Jun. 2014, 2 pages.

* cited by examiner

CLIENT COMPUTING DEVICE HEALTH-RELATED SUGGESTIONS

CROSS REFERENCE TO RELATED APPLICATIONS

This application claims priority to U.S. Provisional Patent Application No. 62/202,119, filed Aug. 6, 2015, the entirety of which is hereby incorporated herein by reference.

BACKGROUND

Improving one's health is a goal that most individuals share, yet many people fall short in achieving. In our busy lives, it can be difficult to make time to visit health care providers for check ups and preventative care. And, many people have trouble following through with resolutions to eat well and exercise. It can also be difficult for people who are not feeling well to understand the causes behind their conditions. Significant challenges exist to improving the health and well-being of both individuals and entire populations, which the technological solutions described herein offer the promise of addressing.

SUMMARY

A client computing device for providing a health-related suggestion and related methods are disclosed herein. In one example, a client computing device comprises a processor and an electronic personal assistant application program executable by the processor. The personal assistant application program is configured to capture user data associated with user activities across a plurality of computer programs. The user data is sent to a personal assistant user data interpretation engine. A health-related suggestion based on at least a subset of the user data and anonymized statistics of a user population retrieved from an aggregated knowledge base is received. The health-related suggestion is displayed on a display associated with the client computing device.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The present disclosure relates to an electronic personal assistant application program that generates and delivers health-related suggestions to users. Before discussing the present disclosure in detail, example infrastructures supporting the technology will first be described.

Figure 1:
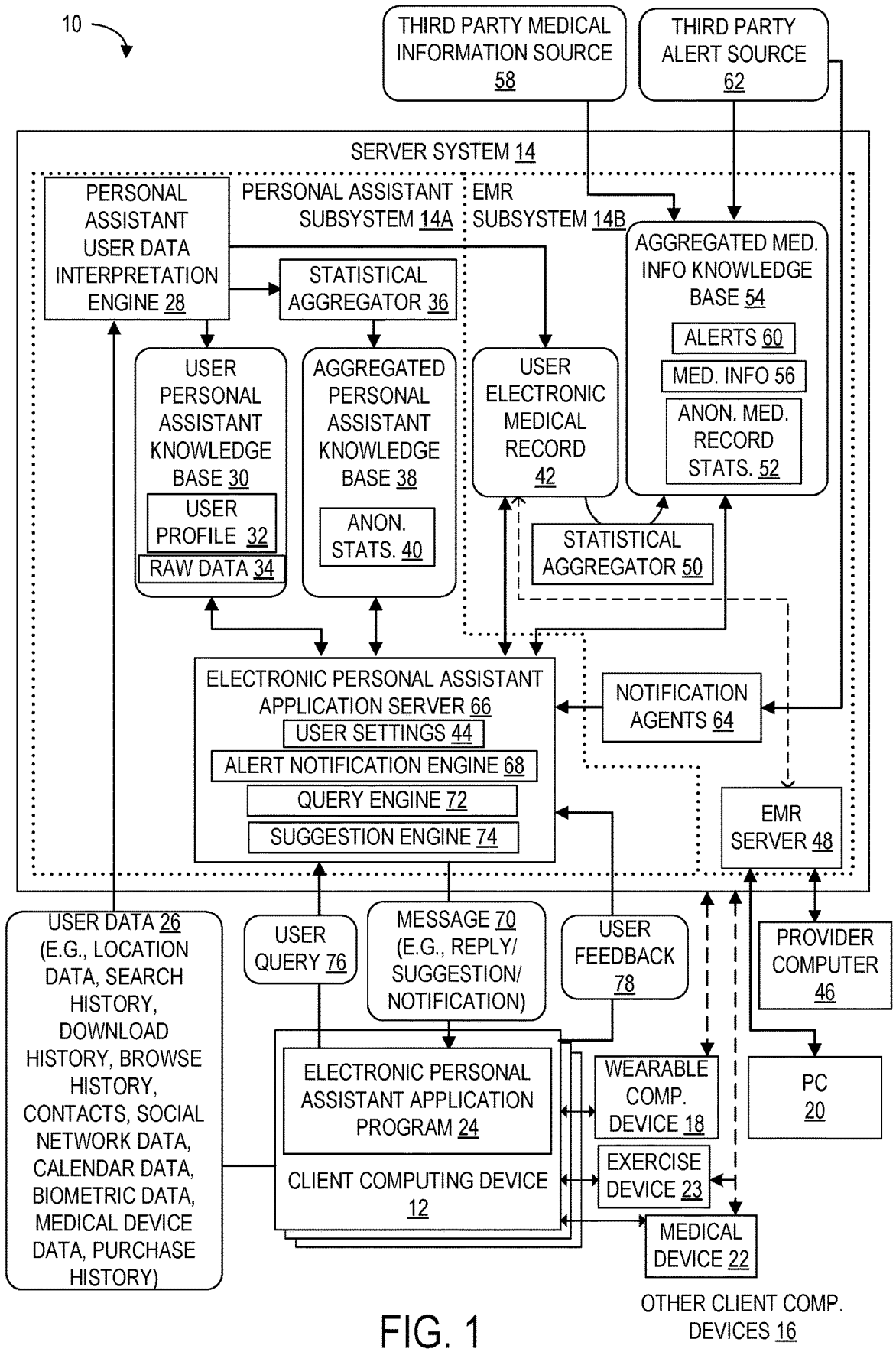
FIG. 1 shows a shows an example computing system according to an embodiment of the present description.

FIG. 1 illustrates a computing system 10 according to one embodiment of the present disclosure. As shown, computing system 10 includes a client computing device 12, which, for example, may take the form of a smart phone or tablet computing device, configured to communicate via a computer network with a server system 14. Computing system 10 may also include other client computing devices 16 configured to communicate with the server system directly through a network connection or indirectly through the client computing device 12. The other client computing devices 16 may include a wearable computing device 18, which may take the form of a wrist mounted device or head mounted device, a personal computer 20, which may take the form of a laptop or desktop computer, a computerized medical device 22, such as a computerized pulse oximeter, electronic inhaler, electronic insulin delivery device, electronic blood sugar monitor, electronic blood pressure monitor, etc., and a computerized exercise device 23, such as a stationary bicycle trainer, rowing machine, treadmill, etc. Wearable computing devices may also include sensors embedded in clothing (t-shirts, undergarments, etc.), or mounted to other body parts (e.g., a finger or ear lobe). Also envisaged are IOT devices not worn directly on the body, but arranged in physical proximity to the user. Such devices may allow measurement of biometric and other data. Examples include cameras, far-infrared thermal detectors, and under-the-mattress sleep sensors, etc. Herein, where functions of the client computing device 12 are described, it will be appreciated that any of the other client computing devices 16 may function in the same manner, unless the specific form factor of the device is mentioned explicitly.

Client computing device 12 is configured to execute an electronic personal assistant application program 24. It will be appreciated that other instances of the electronic personal assistant application program 24 may be executed on the other client computing devices 16 as well, all of which are associated with a user account on server system 14. Subject to authorization by a user, the electronic personal assistant program is configured to passively monitor various user data 26 on the client computing device 12 and other client computing devices 16, such as location data, search history, download history, browsing history, contacts, social network data, calendar data, biometric data, medical device data, purchase history, etc. In some examples, user data 26 may be generated by or otherwise associated with user activities across a plurality of programs. In some examples one or more of these programs may be executed on the client computing device 12. In some examples one or more of such programs may be executed on another computing device, and the user may interact with such programs via the client computing device 12.

Specific examples of these various types of user data 26 will now be described. Location data may include for example, GPS coordinate data (latitude and longitude) obtained by a GPS receiver implemented on any client computing device, an identifier such as an IP address and/or Wi-Fi access point identifier that can be resolved to a generalized geographic location, a user check-in at a location via a social network program, etc. Search history may include a user's search queries entered in a search engine interface such as a browser displaying a search engine web page or a search application executed on the client computing device. The download history may include, for example, applications installed or files downloaded from a download website, including songs, videos, games, etc. Each of these applications and files may have metadata associated with them, such as categories, genres, etc., which can be used to build user profile 32, discussed below. The browse history may include a list of websites, and particular pages within websites visited by a user using a browser executed on the client computing device. The browse history may also include in-application browsing of application specific databases, such as a shopping application that is configured to enable a user to browse a vendor's catalog. The contacts include names and contact information for individuals or organizations saved in a user contact database on client computing device 12, or retrieved from an external site, such as a social network website. The social network data may include a user's friends list, a list of social network entities "liked" by the user, check-ins made by the user at locations via a social network program, posts written by the user, etc. Biometric data may include a variety of data sensed by sensors on client computing device 12 or other client computing devices 16, such as pedometer information, heart rate and blood pressure, duration and timing of sleep cycles, body temperature, galvanic skin response, etc. Additional biometric data is discussed below in relation to the wristwatch embodiment of the wearable computing device 18. Medical device data may include data from medical device 22. Such data may include, for example, inhaler usage data from an electronic inhaler device, blood sugar levels from an electronic blood sugar monitor, insulin pumping data from an electronic insulin pump, pulse oximetry data from an electronic pulse oximeter, etc. Purchase history may include information gleaned from an ecommerce transaction between the client computing device 12 and an ecommerce platform, regarding products purchased by a user, including product descriptions, time and date of purchase, price paid, user feedback on those purchases, etc. It will be appreciated that these specific examples are merely illustrative and that other types of user data specifically not discussed above may also be monitored.

User data 26 is transmitted from the electronic personal assistant application program 24 to the personal assistant user data interpretation engine 28 executed on server system 14. The personal assistant user data interpretation engine 28 performs various operations on the received user data 26, including storing copies of the raw data 34 of the user data 26 in the user personal assistant knowledge base 30 (a database stored in a mass storage device of the server system 14), making inferences based upon the received user data 26 to thereby fill out a user profile 32 for the user, passing some of the user data 26 for each individual user to a statistical aggregator 36, which computes anonymized statistics 40 based on information received from all users of the server system and stores these anonymized statistics in the aggregated personal assistant knowledge base 38 (another database stored in a mass storage device of the server system 14), and passing a filtered subset of the user data to the user electronic medical record 42 based on user settings 44 in the electronic personal assistant application server 66.

As a specific example, the user profile may include inferred data from the user data 26 regarding the demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, and health benefits information.

User electronic medical records are secure electronic records stored in a database in a mass storage device associated with server system 14. Typically, data is populated within the electronic medical record for each user by a healthcare provider using provider computer 46. Provider computer 46 interacts with secure electronic medical record server 48, which in turn stores and retrieves the data in the user electronic medical record 42. The EMR server 48 is configured to communicate with secure channels (e.g., HTTPS and TLS), and store data in encrypted form. Further, the EMR server 48 is configured to control access to the user electronic medical record such that only authorized healthcare providers can make entries and alter certain provider-controlled fields of the medical record. Provider controlled fields may include many of the same types of data included in the user profile, but which are confirmed with the user by the provider and entered into the medical record by the provider rather than inferred by computer algorithms, thus the accuracy and provenance of the data in the EMR is greater than the user profile 32. Specific examples of data that may be stored in the provider controlled portion of the user electronic medical record include demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, health benefits information, and genetic profile of the user.

Other fields within the user electronic medical record are user-controlled, such that authorized persons including the patient who is the subject of the medical record can make entries in the medical record. Further, the user may adjust user settings 44 to allow the personal assistant user data interpretation engine 28 to programmatically update the user-controlled fields of the user electronic medical record with either raw data 34 or inferred data in user profile 32 derived from user data 26. In this way the medical record may be programmatically updated to include medical device data such as inhaler usage, blood sugar monitoring levels, insulin pump usage, etc., and biometric data such as heart rate and blood pressure history, sleep history, body temperature, galvanic skin response, etc.

A statistical aggregator 50 is provided to generate anonymized medical records statistics 52 based on the stored user electronic medical records of an entire user population or a predefined cohort thereof, and store the anonymized medical record statistics in aggregated medical information knowledge base 54. In this manner, statistics may be stored for all manner of user populations. For example, a percentage of the population who live within a defined geographical region and who have been diagnosed with a certain medical condition (such as H1N1 influenza) may be identified, and data about this subset of persons may be compared to identify risk factors. The statistical aggregator may also process statistics related to steps, calories, activity level, sleep and exercise habits of an entire population, or a predefined cohort thereof, which later may be used for comparative insights on user behaviors.

Medical information 56 aggregated from third party medical information sources 58 and alerts 60 from third party alert sources 62 are also stored within the aggregated medical information knowledge base 54. In other implementations, the aggregated medical information need not be stored per se, provided it can be accessed in real time. Examples of medical information 56 includes current practices and procedures, differential diagnostic information that medical professionals use to distinguish between possible diagnoses for a given set of symptoms, descriptions of medical conditions including diseases and syndromes, and their associated symptoms, information on standardized medical screenings recommended by age and gender of the patient, information on standardized vaccination schedules recommended for children and adults, medical conditions associated with certain genetic profiles, drug information such as doses, allergens, potential interactions, etc. Examples of third party medical sources 58 include medical publishers and professional medical organizations. Examples of alerts include reports from governmental and non-governmental organizations that report the occurrence of disease in particular geographic regions, including the boundaries of the geographic region, the type of disease reported, the number of persons affected, the mortality statistics associated with the affected persons, information about the incubation period and period of contagiousness for the disease, and any travel restrictions or recommended restrictions to the affected geographic region, etc. These alerts may be from a country's center for disease control, state or county health department, a company, a school district, a hospital, etc.

Alerts 60 from third party alert sources 62 may also be received by notification agents 64 within server system 14, which in turn instruct an alert notification engine 68 of the electronic personal assistant application server 66 to send a message 70 in the form of a push notification featuring the content of the alert 60 to the electronic personal assistant application program 24 executed on the client device 12, or multiple client devices running the personal assistant application program. In one specific example, the alert may be sent only to users who have recently traveled to the affected area, or who the data interpretation engine 28 infers will soon travel to the affected area, to inform the person of a disease outbreak in the particular geographic area. In another example, the alert may be sent only to persons who have been detected by the system as being within a threshold distance of a person who has been diagnosed with a contagious disease throughout the period which the diagnosed person was contagious. Such a notification can be made while maintaining the privacy of the diagnosed individual.

In addition to push notifications for alerts 60, electronic personal assistant application server 66 also includes a query engine 72 configured to respond with messages 70 in the form of replies to a user query 76 received from the electronic personal assistant application program, and a suggestion engine 74 configured to proactively send messages 70 in the form of suggestions to the electronic personal assistant application programs based on user settings 44 and a set of programmatic suggestion rules. In one specific example, the client computing device 12 may display a query interface, such as a text box or voice prompt, and the user may type in a query or speak a query to the client computing device, such as "What could be causing this headache?" This user query 76 is sent to the query engine 72, which performs searches in each of the databases 30, 38, 42, and 52, subject to user authorizations via settings 44 to conduct searches using each of these databases. Results are returned from each database relating to causes for headaches. The user profile may indicate that the user is a "coffee drinker," and the purchase history and location history may indicate the user visits coffee shops on average 2-3 times a day but has not visited a coffee shop in the past 2 days. The anonymized statistics may indicate that "coffee drinkers" report having headaches more often than the general population. The user electronic medical record may include a prior doctor visit in which the complained of a headache after suffering from heatstroke. The aggregated medical information knowledge base may contain medical information that indicates that heatstroke is typically experienced when a user sweats profusely in extremely hot temperatures and experiences fast heartbeat. The raw data 34 from the user profile may show extremely hot ambient temperatures but may not show galvanic skin response indicative of sweating nor a pulse indicative of fast heartbeat.

In some examples, anonymized statistics may be processed by machine learning algorithms executed on the electronic personal assistant application server 66. The machine learning algorithms may apply weightings and rank a plurality of health-related suggestions, such as possible causes of the headache in the present example. In this example, the query engine would apply weightings that result in ranking the possible causes of the headache as (1) caffeine withdrawal, and (2) heat exhaustion, and display this information to the user with a recommendation to seek the advice of a health care professional.

The electronic personal assistant application program may solicit user feedback 78 from the user regarding the effectiveness or appropriateness of the message 70, which may in turn be transmitted back to the electronic personal assistant application server 66, and used by machine learning algorithms executed thereon to continually improve the weightings and logic by which the electronic personal assistant application server 66 makes decisions regarding the content to send to the client computing device in message 70. Continuing with the above example, if the user's headache was in fact caused by caffeine withdrawal, as diagnosed during a visit to a healthcare professional, the user might enter feedback indicating the first displayed search result was correct, and that information could then be passed to the query engine 72 as a confirmed result for machine learning algorithms that strengthen the weightings upon which the ranking was based when such confirmations are received.

Figure 2A:
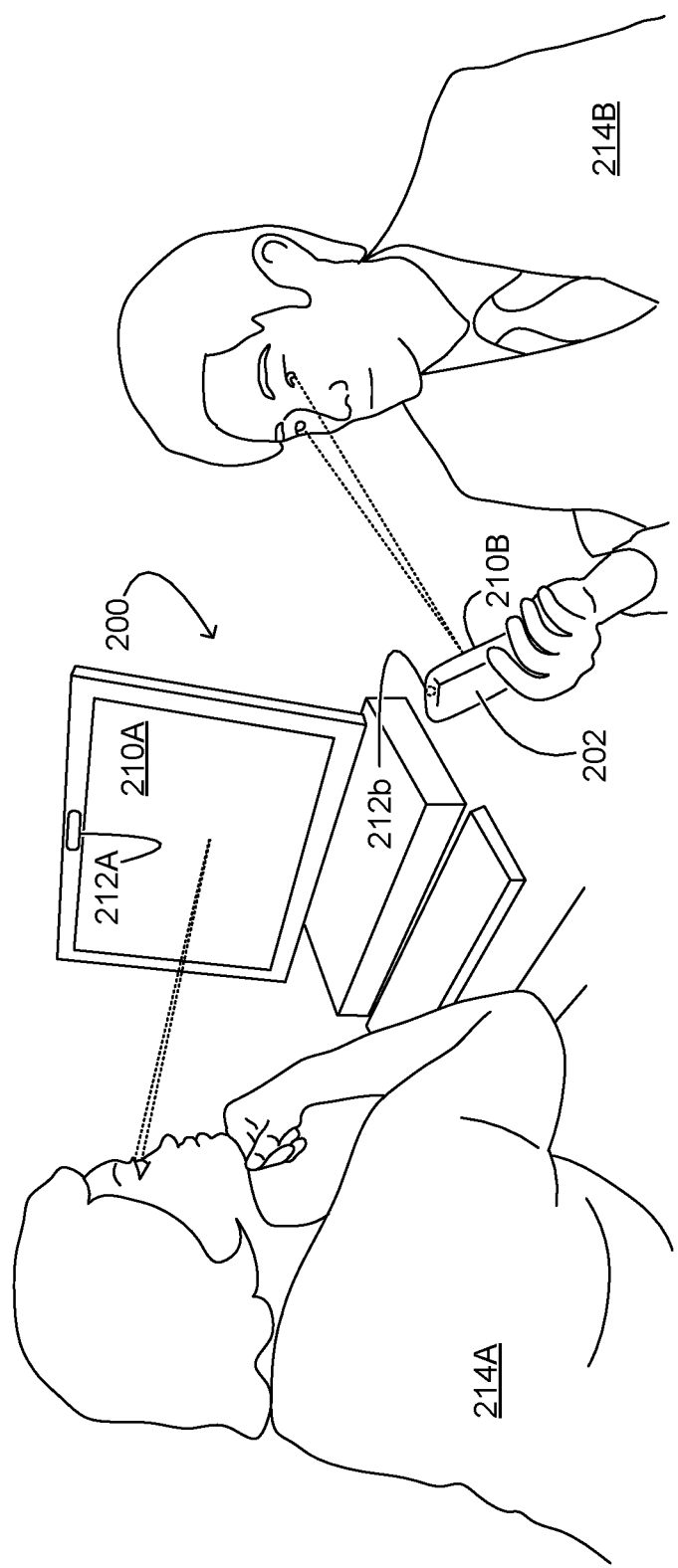
FIGS. 2A and 2B show aspects of various example implementation environments for providing health-related suggestions according to embodiments of the present description.
Figure 2B:
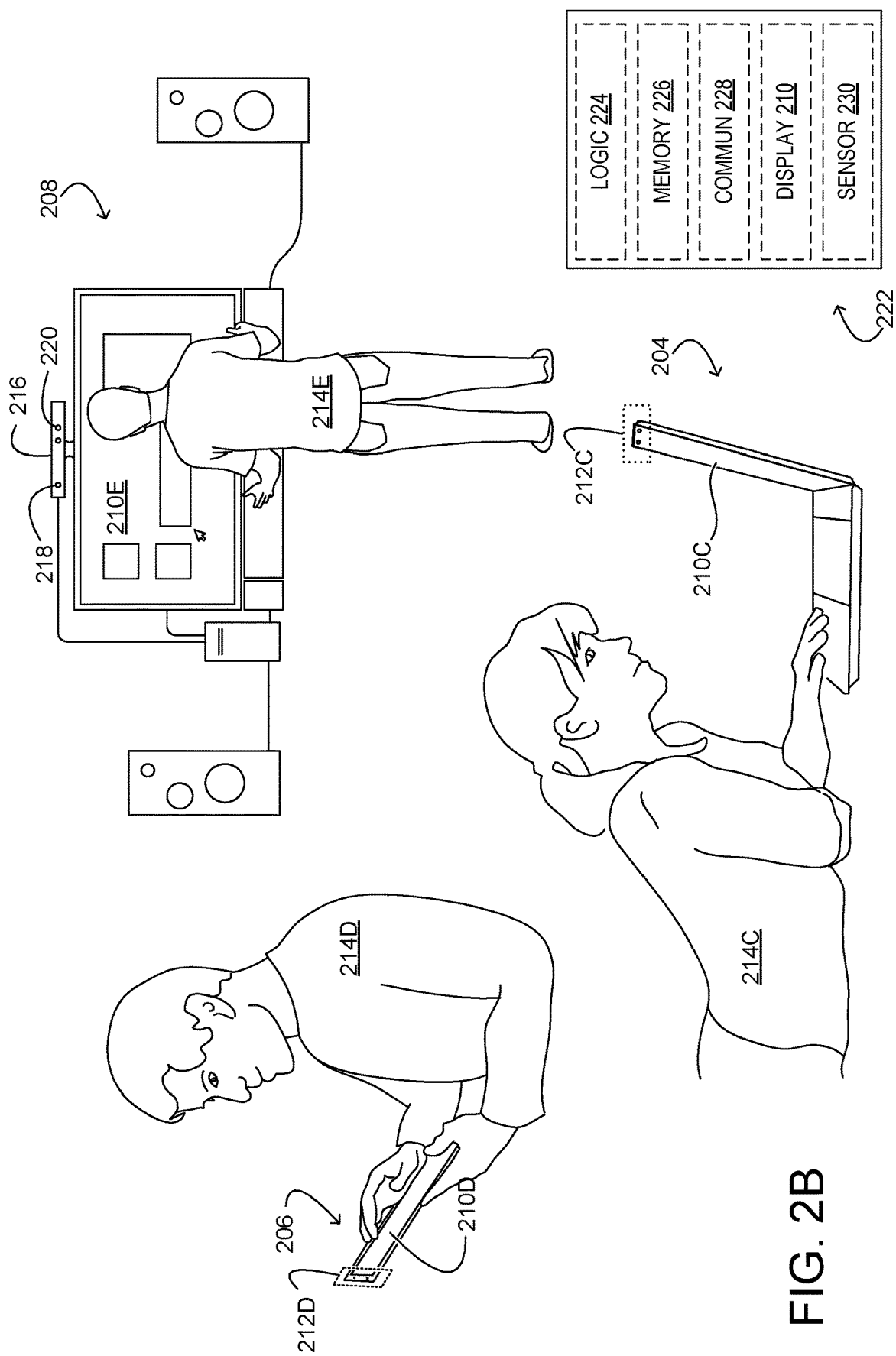

FIGS. 2A and 2B show aspects of various example implementation environments for providing a health-related suggestion. FIG. 2A shows a personal computer, such as PC 20 from FIG. 1, in the form of desktop computer 200. FIG. 2A also shows a client computing device 12 in the form of smartphone 202.

Other personal computers and client computing devices are shown in FIG. 2B. This drawing shows laptop computer 204, tablet computer 206, and home-entertainment system 208. The illustrated desktop, laptop, smartphone, and tablet computer systems each include a display 210, and may also include an integrated vision system 212 configured to image the user's face, track the user's gaze or otherwise sense a facial or ocular condition of the user 214. Each vision system may include at least one camera. The home-entertainment system 208 includes a large-format display 210E and high-fidelity vision system 216 for user face or posture detection. The high-fidelity vision system may include a color camera 218, a time-of-flight depth-sensing camera 220, and an associated infrared illuminator.

Each of the above personal computers and client computing devices may share at least some of the features of compute system 222, also shown in FIG. 2B. The compute system includes a logic machine 224 operatively coupled to a computer-memory machine 226, to display 210, communication machine 228, and one or more sensors 230. These and other aspects of compute system 222 will be described hereinafter.

Figure 3A:
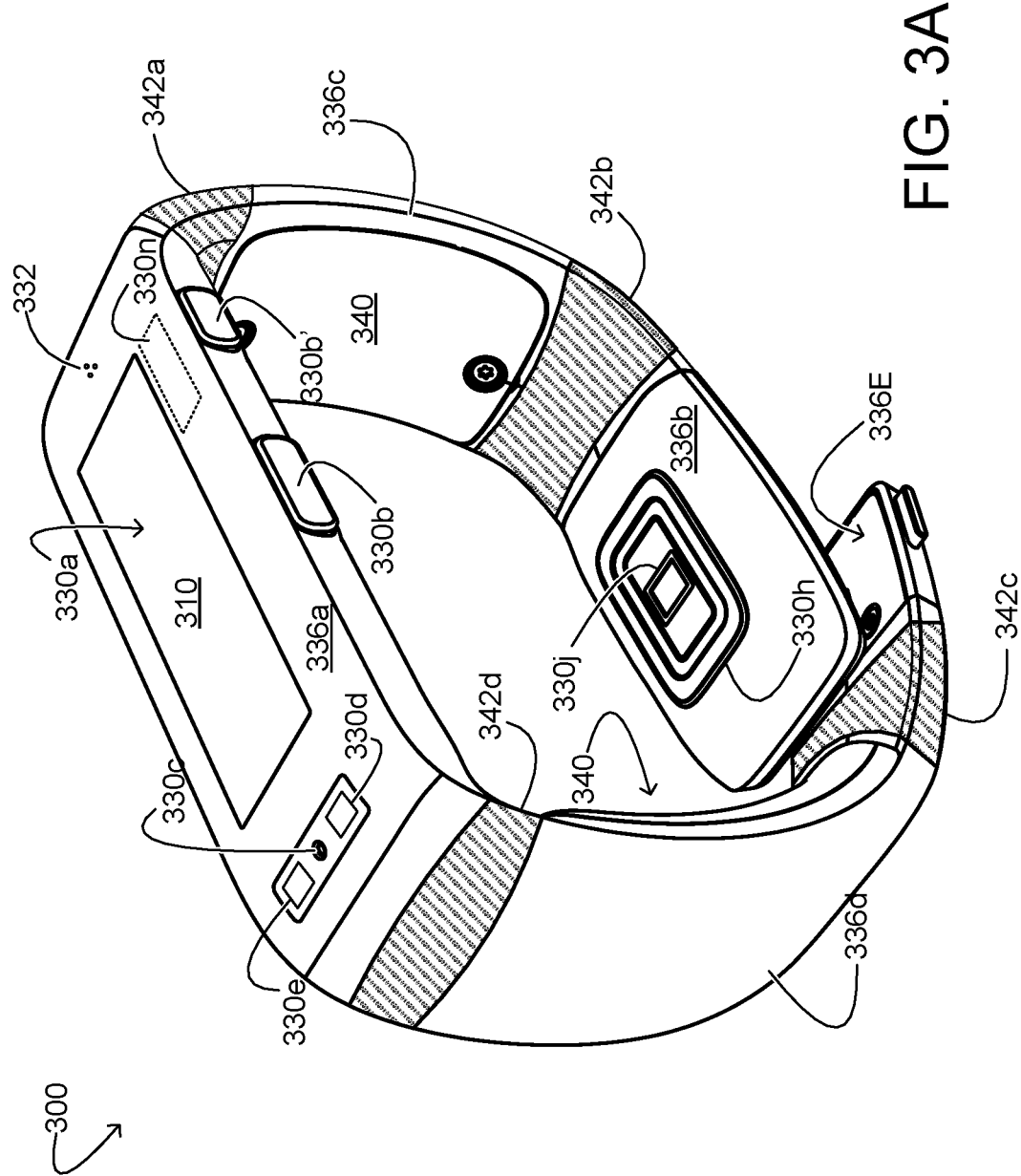
FIGS. 3A and 3B show aspects of one example of a wearable computing device.
Figure 3B:
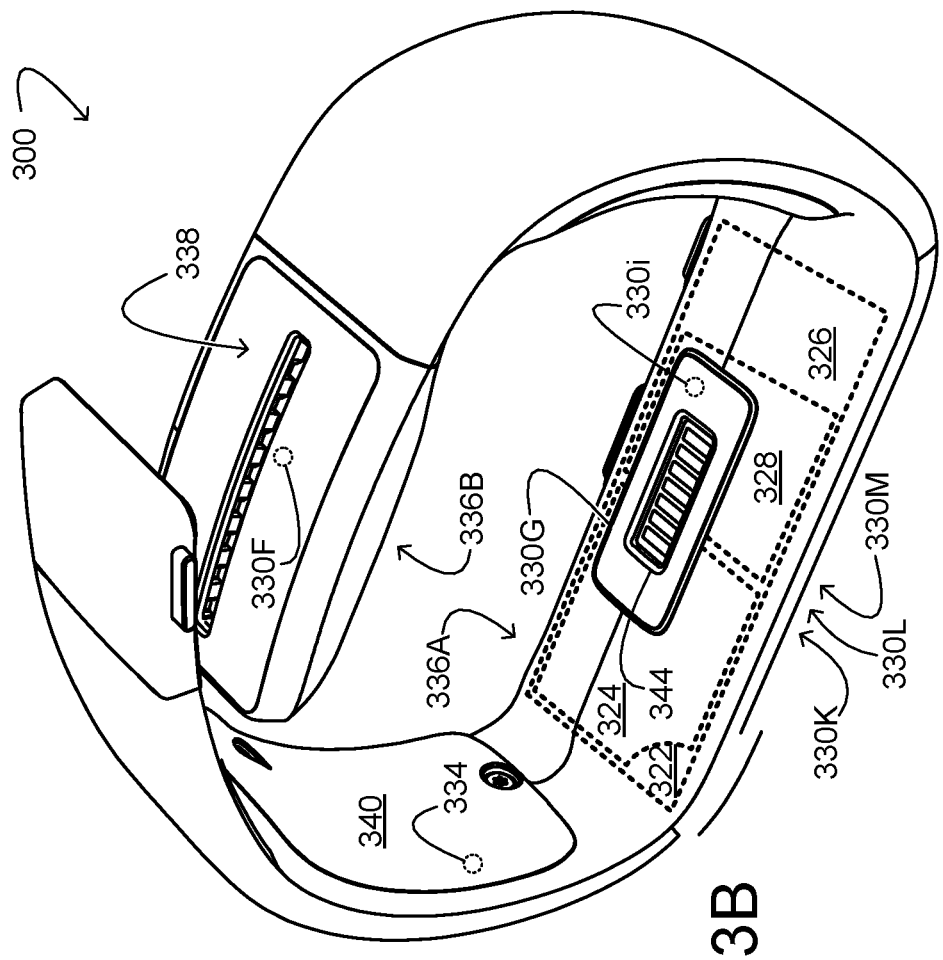

FIGS. 3A and 3B show one example of a wearable computing device, such as wearable computing device 18 from FIG. 1. The illustrated device takes the form of a composite band 300. In one implementation, a closure mechanism enables facile attachment and separation of the ends of the composite band, so that the band can be closed into a loop and worn on the wrist. In other implementations, the device may be fabricated as a continuous loop resilient enough to be pulled over the hand and still conform to the wrist. Alternatively, the device may have an open-bracelet form factor in which ends of the band are not fastened to one another. In still other implementations, wearable electronic devices of a more elongate band shape may be worn around the wearer's bicep, waist, chest, ankle, leg, head, or other body part.

As shown in the drawings, composite band 300 may include various functional electronic components: a compute system 322, display 310, loudspeaker 332, haptic motor 334, communication machine 328, and various sensors 330. In the illustrated implementation, functional electronic components are integrated into the several rigid segments of the band—viz., display-carrier module 336A, pillow 336B, energy-storage compartments 336C and 336D, and buckle 336E. In the illustrated conformation of composite band 300, one end of the band overlaps the other end. Buckle 336E is arranged at the overlapping end of the composite band, and receiving slot 338 is arranged at the overlapped end.

The functional electronic components of wearable composite band 300 draw power from one or more energy-storage components 340. A battery—e.g., a lithium ion battery—is one type of energy-storage electronic component. Alternative examples include super- and ultra-capacitors. To provide adequate storage capacity with minimal rigid bulk, a plurality of discrete, separated energy-storage components may be used. These may be arranged in energy-storage compartments 336C and 336D, or in any of the rigid segments of composite band 300. Electrical connections between the energy-storage components and the functional electronic components are routed through flexible segments 342.

In general, energy-storage components 340 may be replaceable and/or rechargeable. In some examples, recharge power may be provided through a universal serial bus (USB) port 344, which includes the plated contacts and a magnetic latch to releasably secure a complementary USB connector. In other examples, the energy-storage components may be recharged by wireless inductive or ambient-light charging.

In composite band 300, compute system 322 is housed in display-carrier module 336A and situated below display 310. The compute system is operatively coupled to display 310, loudspeaker 332, communication machine 328, and to the various sensors 330. The compute system includes a computer memory machine 326 to hold data and instructions, and a logic machine 324 to execute the instructions.

Display 310 may be any type of display, such as a thin, low-power light emitting diode (LED) array or a liquid-crystal display (LCD) array. Quantum-dot display technology may also be used. Suitable LED arrays include organic LED (OLED) or active matrix OLED arrays, among others. An LCD array may be actively backlit. However, some types of LCD arrays—e.g., a liquid crystal on silicon, LCOS array—may be front-lit via ambient light. Although the drawings show a substantially flat display surface, this aspect is by no means necessary, for curved display surfaces may also be used. In some use scenarios, composite band 300 may be worn with display 310 on the front of the wearer's wrist, like a conventional wristwatch.

Communication machine 328 may include any appropriate wired or wireless communications componentry. In FIGS. 2A and 2B, the communications facility includes the USB port 344, which may be used for exchanging data between composite band 300 and other computer systems, as well as providing recharge power. The communication facility may further include two-way Bluetooth, Wi-Fi, cellular, near-field communication, and/or other radios. In some implementations, the communication facility may include an additional transceiver for optical, line-of-sight (e.g., infrared) communication.

In composite band 300, touch-screen sensor 330A is coupled to display 310 and configured to receive touch input from the wearer. In general, the touch sensor may be resistive, capacitive, or optically based. Push-button sensors (e.g., microswitches) may be used to detect the state of push buttons 330B and 330B', which may include rockers. Input from the push-button sensors may be used to enact a home-key or on-off feature, control audio volume, microphone, etc.

FIGS. 3A and 3B show various other sensors 330 of composite band 300. Such sensors include microphone 330C, visible-light sensor 330D, ultraviolet sensor 330E, and ambient-temperature sensor 330F. The microphone provides input to compute system 322 that may be used to measure the ambient sound level or receive voice commands from the wearer. Input from the visible-light sensor, ultraviolet sensor, and ambient-temperature sensor may be used to assess aspects of the wearer's environment.

FIGS. 3A and 3B show a pair of contact sensors—charging contact sensor 330G arranged on display-carrier module 336A, and pillow contact sensor 330H arranged on pillow 336B. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. In the illustrated configuration, the separation between the two contact sensors provides a relatively long electrical path length, for more accurate measurement of skin resistance. In some examples, a contact sensor may also provide measurement of the wearer's skin temperature. In the illustrated configuration, a skin temperature sensor 330I in the form a thermistor is integrated into charging contact sensor 330G, which provides direct thermal conductive path to the skin Output from ambient-temperature sensor 330F and skin temperature sensor 330I may be applied differentially to estimate of the heat flux from the wearer's body. This metric can be used to improve the accuracy of pedometer-based calorie counting, for example. In addition to the contact-based skin sensors described above, various types of non-contact skin sensors may also be included.

Arranged inside pillow contact sensor 330H in the illustrated configuration is an optical pulse-rate sensor 330J. The optical pulse-rate sensor may include a narrow-band (e.g., green) LED emitter and matched photodiode to detect pulsating blood flow through the capillaries of the skin, and thereby provide a measurement of the wearer's pulse rate. In some implementations, the optical pulse-rate sensor may also be configured to sense the wearer's blood pressure. In the illustrated configuration, optical pulse-rate sensor 330J and display 310 are arranged on opposite sides of the device as worn. The pulse-rate sensor alternatively could be positioned directly behind the display for ease of engineering.

Composite band 300 may also include inertial motion sensing componentry, such as an accelerometer 330K, gyroscope 330L, and magnetometer 330M. The accelerometer and gyroscope may furnish inertial data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation.

Composite band 300 may also include a global positioning system (GPS) receiver 330N for determining the wearer's geographic location and/or velocity. In some configurations, the antenna of the GPS receiver may be relatively flexible and extend into flexible segment 342A.

Figure 4A:
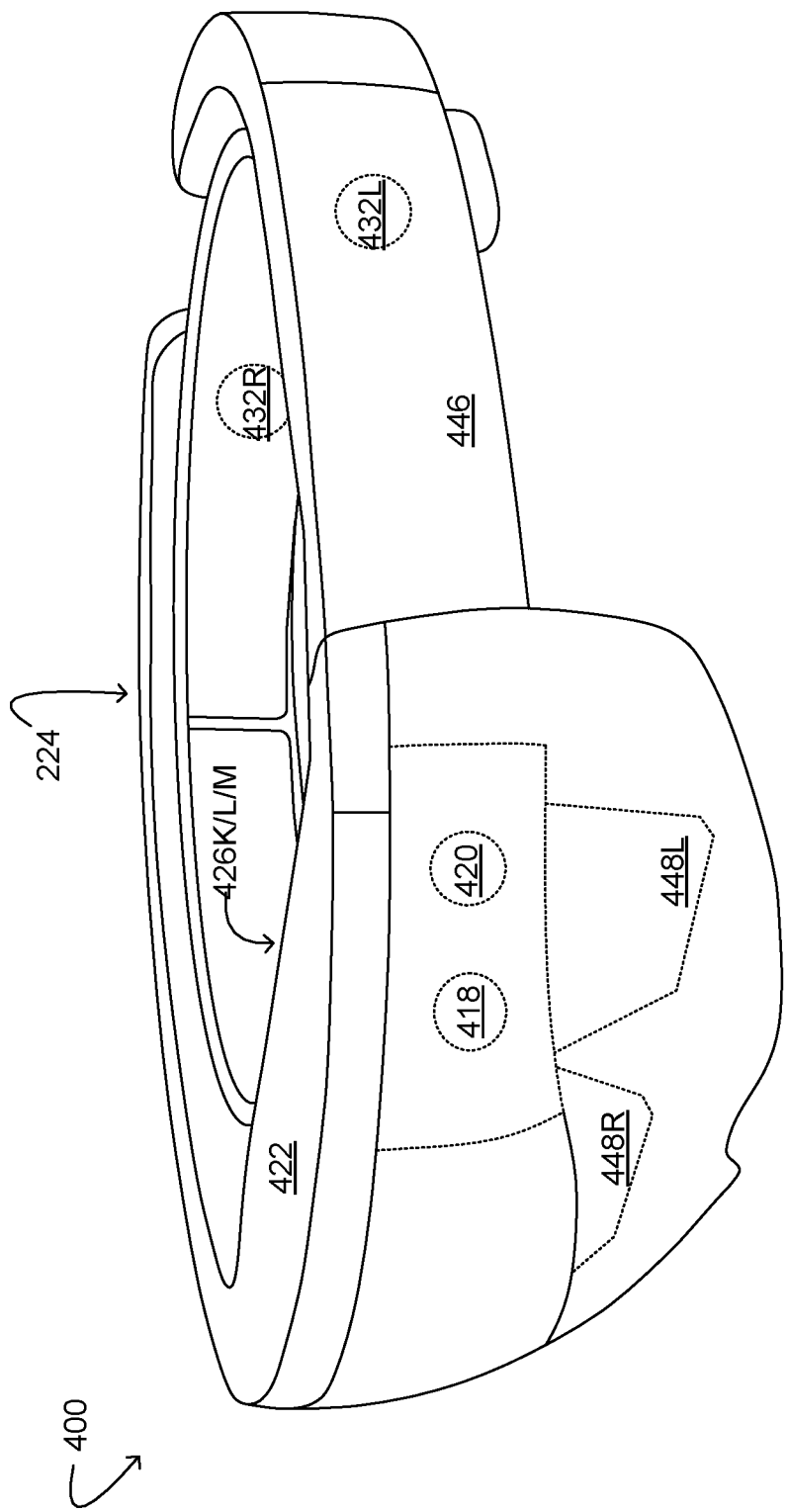
FIG. 4A shows aspects of another example of a wearable computing device.

FIG. 4A shows aspects of an example head-mounted display (HMD) 400 to be worn and used by a wearer. The illustrated display system includes a frame 446. The frame supports stereoscopic, see-through display componentry, which is positioned close to the wearer's eyes. HMD 400 may be used in augmented-reality applications, where real-world imagery is admixed with virtual display imagery.

HMD 400 includes separate right and left display panels, 448R and 448L, which may be wholly or partly transparent from the perspective of the wearer, to give the wearer a clear view of his or her surroundings. Compute system 422 is operatively coupled to the display panels and to other display-system componentry. The compute system includes logic and associated computer memory configured to provide image signal to the display panels, to receive sensory signal, and to enact various control processes described herein. HMD 400 may include an accelerometer 426K, gyroscope 426L, and magnetometer 426M, stereo loudspeakers 432R and 432L, a color camera 418, and a time-of-flight depth camera 420.

Figure 4B:
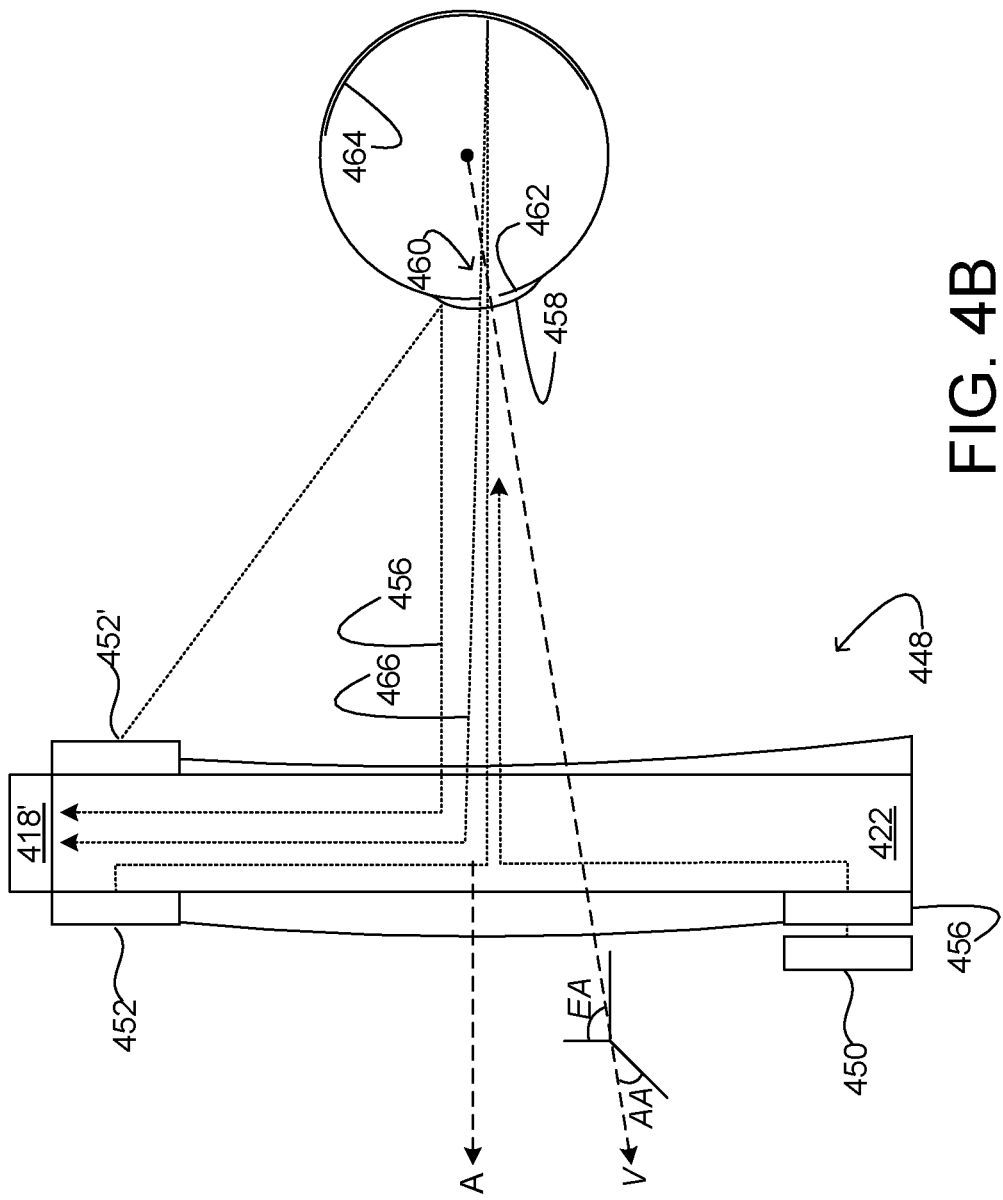
FIG. 4B shows aspects of a display panel of a wearable computing device.

FIG. 4B shows selected aspects of right or left display panel 448 (448R, 448L) in one, non-limiting embodiment. The display panel includes a backlight 450 and a liquid-crystal display (LCD) type microdisplay 410. The backlight may include an ensemble of light-emitting diodes (LEDs)—e.g., white LEDs or a distribution of red, green, and blue LEDs. The backlight may be configured to direct its emission through the LCD microdisplay, which forms a display image based on control signals from compute system 422. The LCD microdisplay may include numerous, individually addressable pixels arranged on a rectangular grid or other geometry. In some embodiments, pixels transmitting red light may be juxtaposed to pixels transmitting green and blue light, so that the LCD microdisplay forms a color image. In other embodiments, a reflective liquid-crystal-on-silicon (LCOS) microdisplay or a digital micromirror array may be used in lieu of the LCD microdisplay of FIG. 4B. Alternatively, an active LED, holographic, or scanned-beam microdisplay may be used to form right and left display images. Although the drawings show separate right and left display panels, a single display panel extending over both eyes may be used instead.

Display panel 448 of FIG. 4B includes an eye-imaging camera 418', an on-axis illumination source 452 and an off-axis illumination source 454. Each illumination source emits infrared (IR) or near-infrared (NIR) illumination in a high-sensitivity wavelength band of the eye-imaging camera. Each illumination source may comprise a light-emitting diode (LED), diode laser, discharge illumination source, etc. Through any suitable objective-lens system, eye-imaging camera 418' detects light over a range of field angles, mapping such angles to corresponding pixels of a sensory pixel array. Compute system 422 may be configured to use the output from the eye-imaging camera to track the gaze axis V of the wearer, as described in further detail below.

On- and off-axis illumination serve different purposes with respect to gaze tracking. As shown in FIG. 4B, off-axis illumination can create a specular glint 456 that reflects from the cornea 458 of the wearer's eye. Off-axis illumination may also be used to illuminate the eye for a 'dark pupil' effect, where pupil 460 appears darker than the surrounding iris 462. By contrast, on-axis illumination from an IR or NIR source may be used to create a 'bright pupil' effect, where the pupil appears brighter than the surrounding iris. More specifically, IR or NIR illumination from on-axis illumination source 452 illuminates the retroreflective tissue of the retina 464 of the eye, which reflects the light back through the pupil, forming a bright image 466 of the pupil. Beam-turning optics 468 of display panel 448 enable the eye-imaging camera and the on-axis illumination source to share a common optical axis A, despite their arrangement on the periphery of the display panel.

Digital image data from eye-imaging camera 418' may be conveyed to associated logic in compute system 422 or in a remote computer system accessible to the compute system via a network. There, the image data may be processed to resolve such features as the pupil center, pupil outline, and/or one or more specular glints 456 from the cornea. The locations of such features in the image data may be used as input parameters in a model—e.g., a polynomial model—that relates feature position to the gaze axis V. In embodiments where a gaze axis is determined for the right and left eyes, the compute system may also be configured to compute the wearer's focal point as the intersection of the right and left gaze axes. In some embodiments, an eye-imaging camera may be used to enact an iris- or retinal-scan function to determine the identity of the wearer. In this configuration, compute system 422 may be configured to analyze the gaze axis, among other output from eye-imaging camera 418' and other sensors.

Figure 5:
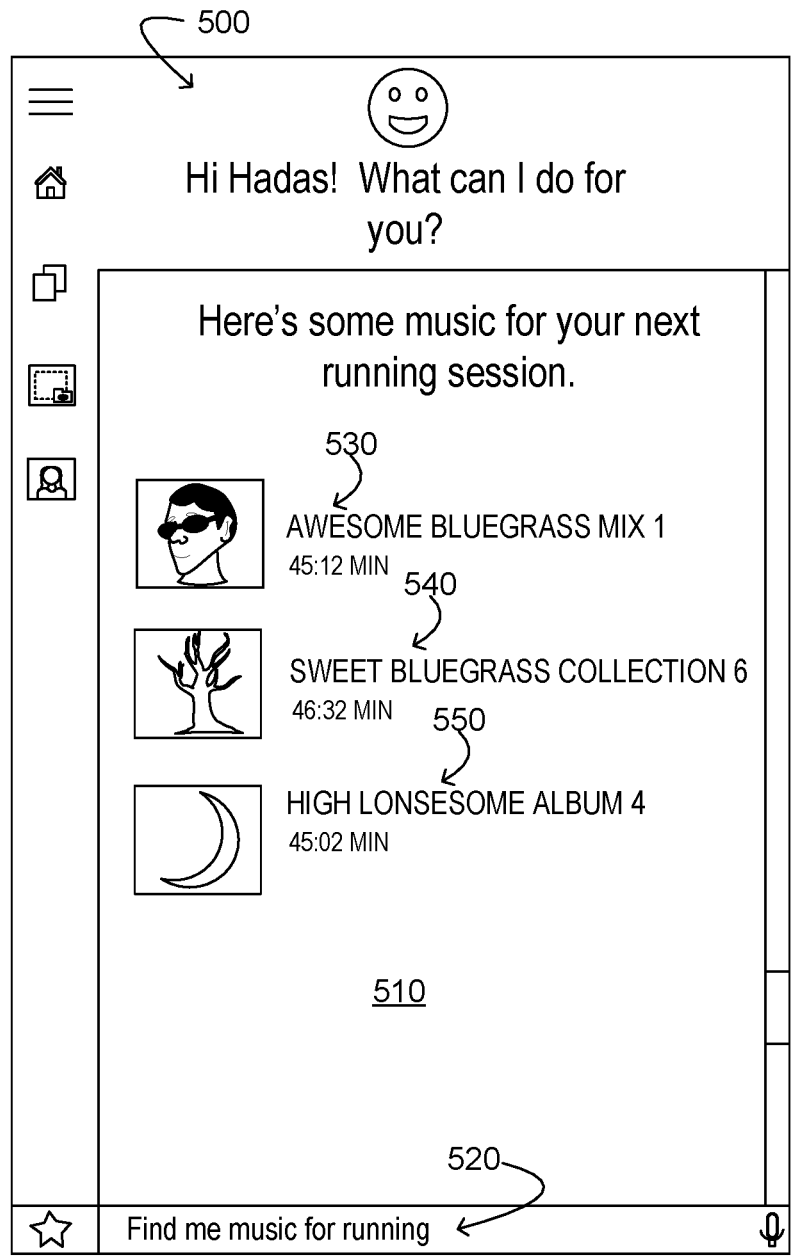
FIG. 5 is a schematic view of a display providing health-related suggestions according to embodiments of the present description.

Turning now to FIGS. 5-12, example use cases of the present disclosure will now be described. FIG. 5 shows an example of a display 500 associated with a client computing device 12, such as smartphone 202. The display 500 is displaying a graphical user interface (e.g., GUI) 510 that may present one or more health-related suggestions to a user of the client computing device. As described in more detail below, health-related suggestions may take the form of messages 70, such as replies to a user query, push notifications and other suggestions.

In the example of FIG. 5 and with reference also to FIG. 1, a user 214 may submit a user query 76 in the form of a verbal request to the smartphone, "Find me music for running", as indicated at 520. As noted above with reference to FIG. 1, the user query 76 may be transmitted via the electronic personal assistant application program 24 to the query engine 72, which may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases. For the above example, the user may be provided with suggested music tracks that are suitable in duration and rhythm to his typical running pattern.

In some examples, the personal assistant user data interpretation engine 28 may analyze at least a portion or a subset of the user data 26 received from the user computing device 12 to make inferences based upon the received user data 26. Such inferences may be provided to the user personal assistant knowledge base 30 to, for example, populate and/or modify the user's profile 32. Such inferences also may be provided to the aggregated personal assistant knowledge base 38 via statistical aggregator 36 and/or to the user electronic medical record 42. In this example and based on at least a subset of the user data, the personal assistant user data interpretation engine 28 determines that the user has a preference for running.

The user's profile 32 also may include data related to a plurality of running sessions that the user has performed. For each run such data may include, for example, one or more of the duration, distance, altitude gain, geographical mapping of the route, average pace, average user heart rate, and maximum user heart rate. In some examples, such data may be collected by a biometric computing device, such as wearable computing device 18, that may transmit such data directly to the personal assistant user data interpretation engine at server system 14 or to client computing device 12, such as smartphone 202.

The user's profile 32 also may include other user preferences that may have been inferred by the personal assistant user data interpretation engine 28. For example, and utilizing user data 26 such as music download history, music-related browse history, music played from a music library on the client computing device 12, etc., the personal assistant user data interpretation engine 28 may determine that the user has preferences for the bluegrass music genre and particular bluegrass artists. Such musical preferences may be stored in the user's profile 32.

In one example and with reference again to FIGS. 1 and 5, in response to the user's query 76, the suggestion engine 74 may select music for a user running session that the user is likely to enjoy or that in the past was determined to encourage the user to run faster or more effectively. The length of the music also may be selected to correspond to the typical duration of the user's running sessions. For example, the average duration of the user's running sessions over the past six months may be 45 minutes and 20 seconds (45:20). The suggestion engine 74 may utilize this average duration to select several music mixes, collections and/or albums from the bluegrass genre that have a total running time close to this average time.

As shown in the example of FIG. 5, the suggestion engine 74 on the electronic personal assistant application server 66 may transmit health-related suggestions in the form of a suggested music mix 530, a suggested music collection 540 and a suggested album 550 to the client computing device 12 for display in the GUI 510. In this manner, the user is presented with particular music selections from a genre she enjoys and that each have a total duration that is close to the average duration of the user's running sessions. The user may simple select one of the suggestions to launch a music player that plays the selected selection.

Figure 6:
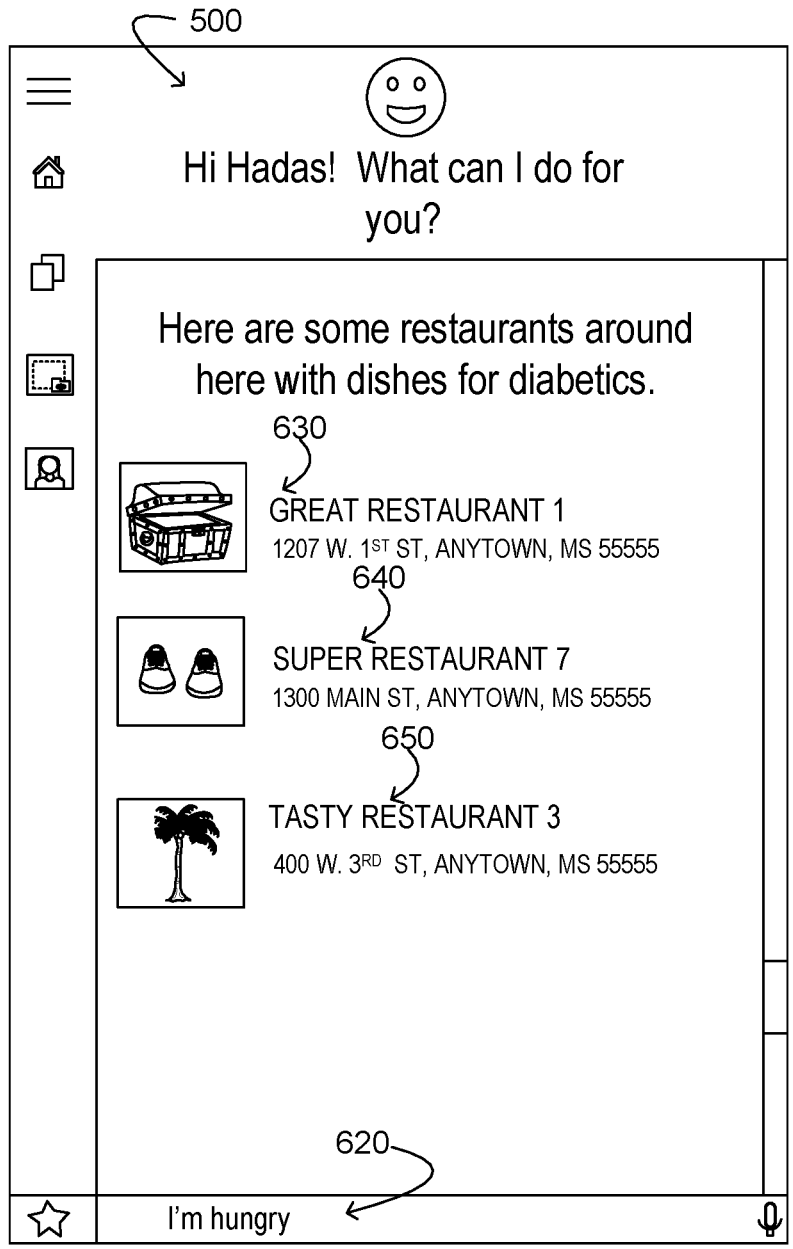
FIG. 6 is a schematic view of a display providing health-related suggestions according to other embodiments of the present description.

With reference now to FIG. 6 and in another example, user 214 may submit a user query 76 in the form of a verbal statement to the smartphone, "I'm hungry", as indicated at 620. As noted above with reference to FIG. 1, the user query 76 may be transmitted via the electronic personal assistant application program 24 to the query engine 72, which may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases.

In this example, the personal assistant user data interpretation engine 28 may analyze user data 26 that includes web searches and browsing history for restaurants and cuisines, purchasing history related to restaurants and cuisines, restaurant reviews and ratings viewed by the user and submitted by the user, and other related user data 26 regarding restaurants. The personal assistant user data interpretation engine 28 may utilize such data to infer restaurants that the user prefers, as well as characteristics of restaurants that the user prefers. Such characteristics may include cuisines, ambience such as children-friendly, romantic, sports bars, etc., price ranges, happy hours, etc.

In response to the query 76, the suggestion engine 74 may access restaurant-related preferences of the user in the user personal assistant knowledge base 30. The suggestion engine 74 also may access user medical information in the user's profile 32 and/or in the electronic medical record 42. As noted above, user medical information may include past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), etc.

In this example, the suggestion engine 74 may determine from the user medical information that the user is diabetic. The suggestion engine 74 also may determine the user's current location from user data 26. Using this data along with the user's preferences related to restaurants, the suggestion engine 74 may transmit via the electronic personal assistant application server 66 health-related suggestions in the form of a three restaurant suggestions 630, 640 and 650 that are within a predetermined distance, such as 1, 2, 5 10 or any suitable number of miles, from the user's current location and that offer dishes for diabetics for display in the GUI 510. In this manner, the user is presented with restaurant suggestions that are selected based on the user's restaurant-related preferences as well as a medical condition of the user.

In some examples, the health-related suggestions in the form of restaurant suggestions also may be based on anonymized statistics of a user population. For example, the suggestion engine 74 also may analyze anonymized medical record statistics 52 from the aggregated medical information knowledge base 54 to determine (or rank) the restaurants at which people with diabetes dined. Such ranking also may be based on a geographic proximity of the restaurant to a location of the user. In some examples restaurants may be identified based at least in part on user population engagement data related to such restaurants, such as browsing histories of the user population of people with diabetes. In other words, restaurants whose websites were visited most by the user population may be weighted or ranked higher.

Figure 7:
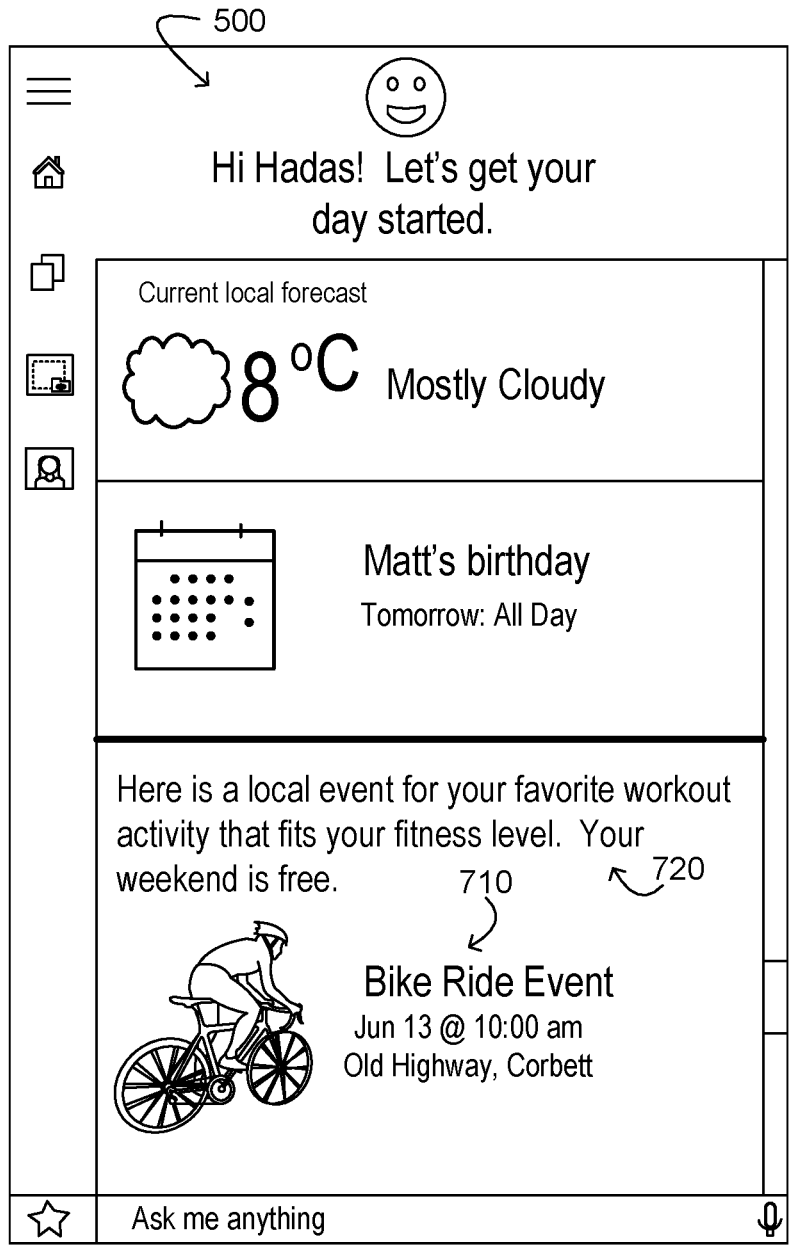
FIG. 7 is a schematic view of a display providing health-related suggestions according to other embodiments of the present description.

With reference now to FIG. 7 and in another example, the electronic personal assistant application program 24 may provide a health-related suggestion in the form of a proactive push notification of a fitness event in which the user may be interested. In some examples the suggestion engine 74 may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases.

In one example, the suggestion engine 74 may determine from data in the user's profile 32 that the user has a health-related goal of engaging in at least 10 hours of aerobic exercise each week. The user's profile 32 may also contain a fitness level of the user. For example, the user may interact with a fitness program located on, for example, the wearable computing device 18. Through the fitness program the user may periodically input the user's fitness level, perhaps on a scale of 1-10, with 1 being the least fit and 10 being the most fit. In other examples, the fitness program may periodically programmatically determine a fitness level of the user. Such fitness level may be transmitted as user data 26 via the electronic personal assistant application program 24 to the personal assistant user data interpretation engine 28 and to the user's profile 32.

In some examples, user biometric data captured by the wearable computing device 18 may be transmitted to the user personal assistant knowledge base 30 as raw data 34. Such biometric data may be transmitted directly from the wearable computing device 18 to the server system 14 or via the electronic persona assistant application program 24 on client computing device 12 as part of user data 26 to the server system 14 and the personal assistant user data interpretation engine 28. Such biometric data may be analyzed by, for example the personal assistant user data interpretation engine 28 to estimate a fitness level of the user. In other examples, such biometric data may be captured by the computerized medical device 22 and similarly transmitted directly from the medical device to the server system 14 or via the electronic personal assistant application program 24 on client computing device 12 as part of user data 26 to the server system 14 and the personal assistant user data interpretation engine 28. In some examples, the electronic personal assistant application program 24 may estimate the user's fitness level. For example and as described above, sensors in the wearable computing device 18 may track the user's pulse-rate and motion. Such data may be used by the electronic personal assistant application program 24 or the personal assistant user data interpretation engine 28 to determine a fitness level of the user.

The personal assistant user data interpretation engine 28 may infer from the user's profile 32 that the user enjoys bike riding and has, for example, performed bike rides in the last month of 25, 30 and 40 miles. The suggestion engine 74 may identify a bike ride event, indicated at 710, that is 30 miles long. The suggestion engine 74 may identify this event from, for example, the user's browse history that includes interest in similar events, or based on its physical proximity to the user's home location. Because the event ride is 30 miles long, and the user has performed bike rides in the last month of 25, 30 and 40 miles, the interpretation engine 28 may determine that this event matches the user's fitness level and is therefore a good event for suggesting to the user. In other examples, the interpretation engine 28 may compare the length of the ride with the user's fitness level to determine whether the ride matches the user's fitness level.

In some examples, an event suggestion also may be based on anonymized statistics of a user population. For example, the anonymized statistics 40 of aggregated user data in the aggregated personal assistant knowledge base 38 may be used to determine that people who rode in a bicycle race last year had an average fitness level of 6 out of 10. The suggestion engine 74 may then match the user's fitness level of 6 to this average fitness level, and in response this ride may be suggested to the user.

In another example, browsing histories of a user population may be analyzed in the anonymized statistics 40 of aggregated user data to estimate a fitness level of members of the user population. For example, a fitness level of a user population member may be estimated based on the fitness-related events for which the member has registered and/or the event websites with which the member has engaged. Using this data, the suggestion engine 74 may then match the user's fitness level to the same or similar fitness level of members of the user population, and correspondingly suggest events to the user in which those members participated in the past and/or whose websites those members engaged with the most. In some examples, the events suggested to the user may be filtered based on a geographic proximity of the event location to a location of the user.

The suggestion engine 74 also may analyze calendar data of the user to determine that the user is available during the time and date of the bike ride event 710. Based on the user's calendar data, the user's location, the user's preference for bike riding, and the user's fitness level, the suggestion engine 74 may provide a health-related suggestion in the form of the bike ride event 710 to the electronic personal assistant application program 24 for display in the GUI 510. In some examples the electronic personal assistant application program 24 may generate for the user and display a customized title 720 for the event that is based on data received from the suggestion engine 74 and/or other data from the user personal assistant knowledge base 30. The customized title 720 may communicate that the event relates to the user's favorite workout activity, fits the user's fitness level, and that the user is available for the event.

Figure 8:
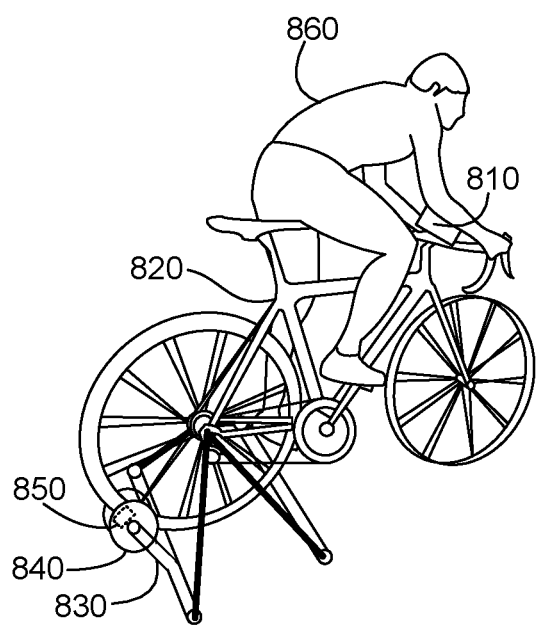
FIG. 8 is a schematic view of a stationary bicycle trainer according to other embodiments of the present description.

With reference now to FIG. 8 and in some examples, the electronic personal assistant application program 24 may be configured to adjust an exercise setting on an exercise device that is communicatively coupled to a client computing device 12 based on a health-related suggestion received from the electronic personal assistant application server 66. In the example of FIG. 8, a client computing device 12 may comprise a display 810 mounted to a bicycle 820. The bicycle 820 may be mounted to a stationary bicycle trainer 830 such that the rear wheel of the bicycle 820 rests in an electronic roller assembly 840.

The roller assembly 840 may comprise a variable resistance device 850 that operates to resist rotation of the rear wheel as the user 860 pedals the bicycle 820. Such variable resistance device 850 may utilize mechanical friction, magnetic resistance, or other suitable technology to provide resistance to rotation of the rear wheel. The resistance imparted by the variable resistance device 850 may be manually and/or programmatically varied to simulate different riding conditions and provide the user 860 with different training regimens, such as a hill climbing workout, interval training workout, recovery day workout, etc.

For example, the user 860 may be entered in an upcoming cycling race that includes several long hill climbs. Information regarding the race may be saved in the user's calendar data. The user's fitness level also may be determined as described above. Based on the race information in the user's calendar data and the user's fitness level, the suggestion engine 74 may access anonymized statistics 40 of aggregated user data in the aggregated personal assistant knowledge base 38 to identify other users who are avid cyclists and who have an equivalent or similar fitness level as the user. Such users who are also entered in the upcoming cycling race also may be identified. By examining, for example, websites visited and download histories of these other users, the suggestion engine 74 may also identify a specific hill training workout program that is popular with and/or has been frequently downloaded by such users.

A health-related suggestion in the form of this specific hill training workout program may be sent to the display 810 mounted to the bicycle 820. The display 810 may be communicatively coupled to the electronic roller assembly 840, and the electronic personal assistant application program 24 of display 810 may utilize the specific hill training workout to programmatically adjust the resistance imparted by the variable resistance device 850 to simulate different hill climbing efforts as the user 860 pedals the bicycle 820.

In some examples, the user 860 may wear a wearable computing device 18, such as the band 300 illustrated in FIGS. 3A and 3B, that receives the specific hill training workout program and is communicatively coupled to the electronic roller assembly 840 to adjust its variable resistance. In some examples, the electronic roller assembly 840 may comprise a client computing device 12, and may be instrumented to receive sensor inputs from a band 300 worn by the user 860. The electronic roller assembly 840 may be communicatively coupled to the server system 14, and may send user data in the form of the sensor inputs to the server system 14. In these examples, the electronic roller assembly 840 may receive and utilize the specific hill training workout program to adjust its variable resistance accordingly.

It will be appreciated that the above example of an electronic roller assembly is one example of an exercise device, and the variable resistance is one example of an exercise setting that may be adjusted on an exercise device. Other examples of exercise devices comprising adjustable exercise settings include electronic rowing machines, treadmills, stair climbers, elliptical trainers, etc.

Figure 9:
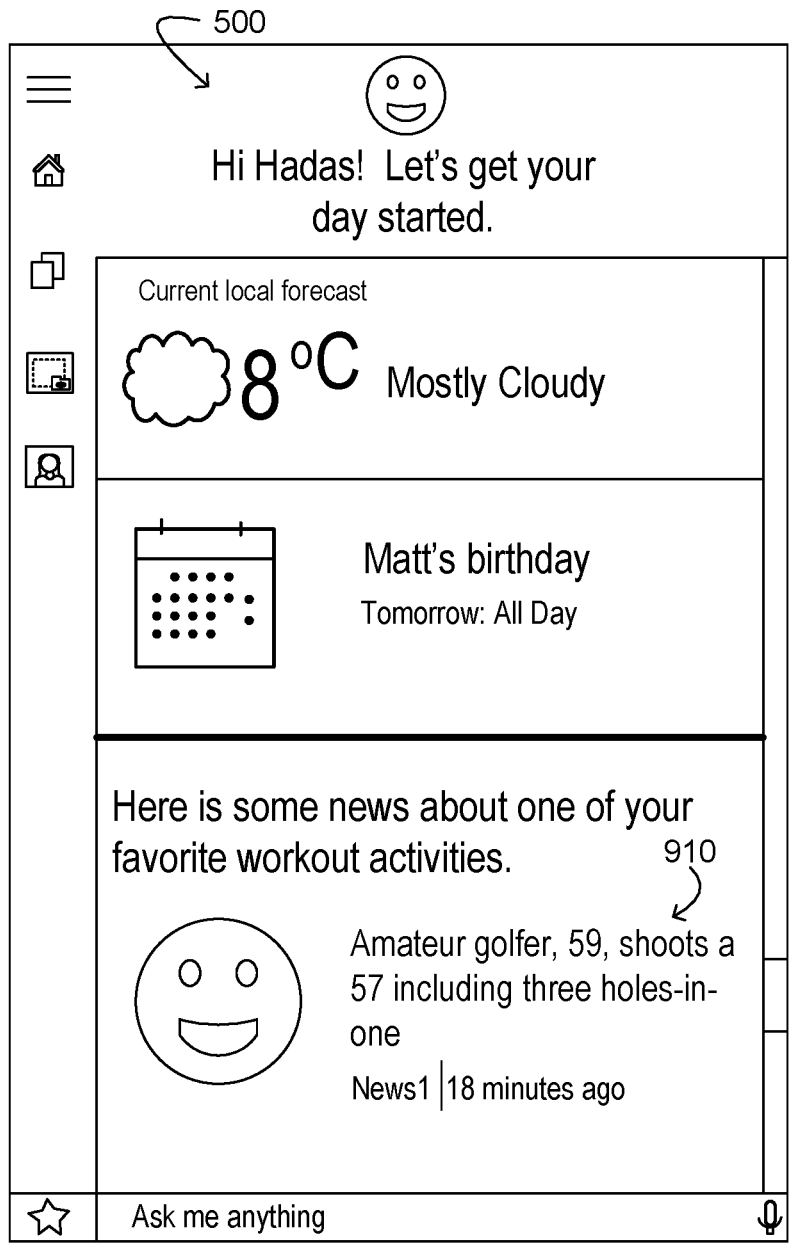
FIG. 9 is a schematic view of a display providing health-related suggestions according to other embodiments of the present description.

With reference now to FIG. 9 and in another example, the electronic personal assistant application program 24 may provide a health-related suggestion in the form of a proactive push notification of a news article in which the user may be interested. In some examples the suggestion engine 74 may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases.

In one example, the suggestion engine 74 may determine from data in the user's profile 32 that the user has a preference for playing golf and that the user has a golf handicap of 7, which corresponds to a numerical measure of a golfer's playing ability. In this example, a golfing handicap of 7 indicates that the user is a skilled amateur golfer. The suggestion engine 74 may search news aggregators and other online content sources for articles and other publications that would be of interest to a person having the user's golfing playing ability (i.e., an amateur golfer having a single-digit handicap).

The suggestion engine 74 may identify a news article that contains content about an amateur golfer. Based on the user's golfing ability, the personal assistant user data interpretation engine 28 may infer that the user may enjoy reading the article. Accordingly, the suggestion engine 74 may transmit to the electronic personal assistant application program 24 a link 910 to the identified news article for display in the GUI 510.

Figure 10:
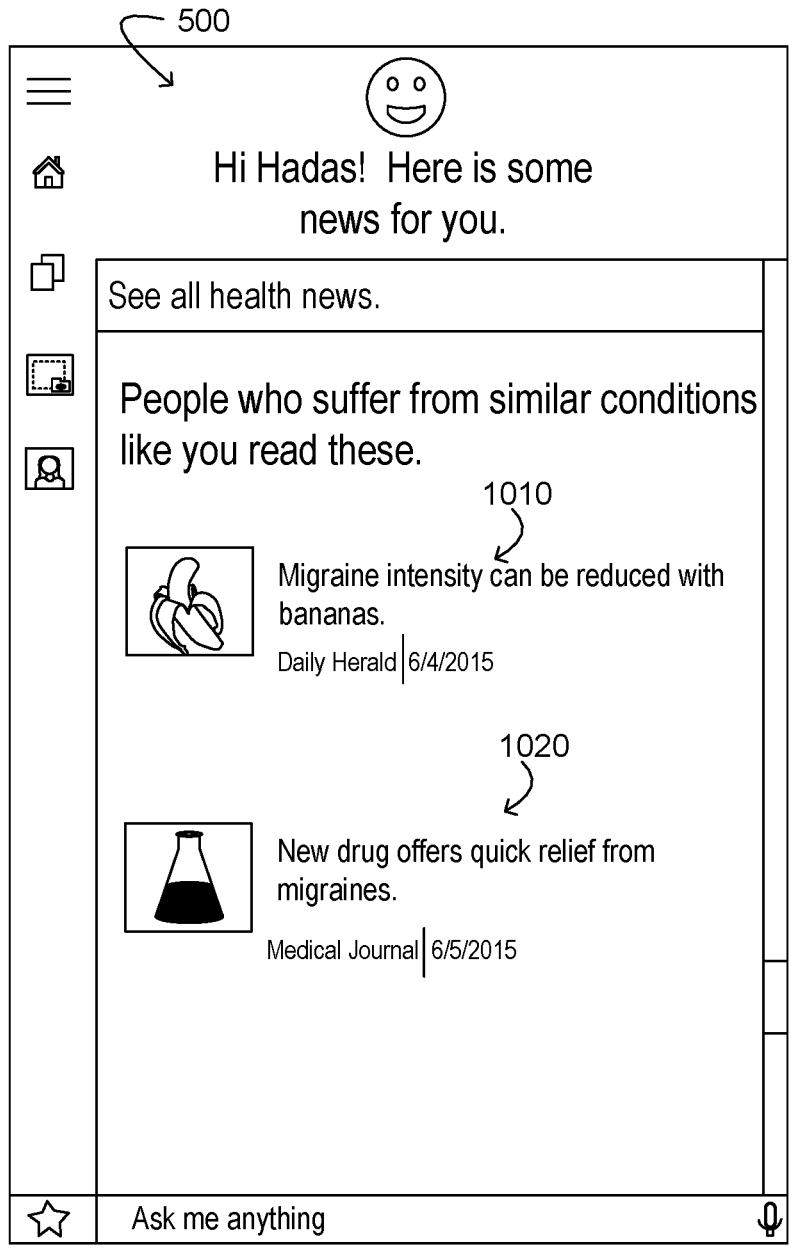
FIG. 10 is a schematic view of a display providing health-related suggestions according to other embodiments of the present description.

With reference now to FIG. 10 and in another example, the electronic personal assistant application program 24 may provide a health-related suggestion in the form of a proactive push notification of a news article, publication or other digital content in which the user may be interested. In some examples the suggestion engine 74 may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases. In the course of such searching the suggestion engine 74 may determine that the user suffers from migraine headaches.

Based on determining that the user suffers from migraine headaches, the suggestion engine 74 may search third party medical information sources 58 and other online content sources for material related to migraine headaches. In the example of FIG. 10, the suggestion engine 74 may identify two articles related to migraine headaches. Accordingly, the suggestion engine 74 may transmit to the electronic personal assistant application program 24 two links 1010 and 1020 to the identified articles for display in the GUI 510.

In some examples, health-related suggestions in the form of article suggestions also may be based on anonymized statistics of a user population. For example, the suggestion engine 74 also may analyze anonymized medical record statistics 52 from the aggregated medical information knowledge base 54 to determine (or rank) popular articles that have been read by people who have experienced migraine headaches. In some examples, articles also may be identified based on user population engagement data related to such articles, such as browsing histories of the user population of people who suffer from migraines.

In one example and based at least on user biometric data received from one or more of the wearable computing device 18 and a computerized medical device 22, the personal assistant user data interpretation engine 28 may infer that the user is currently experiencing a migraine headache. In response to this determination, the suggestion engine 74 may perform a refined search of third party medical information sources 58 and other online content sources for material that may help the user quickly address and perhaps alleviate the migraine headache.

In this example, the suggestion engine 74 may locate the article indicated by link 1010 that suggests that migraine intensity can be reduced by ingesting bananas. The suggestion engine 74 may also analyze the current location of the user to determine that the user is at home. The suggestion engine may further determine from the user's purchasing history in the user personal assistant knowledge base 30 that the user regularly purchases bananas. Accordingly, the suggestion engine 74 may correlate information gleaned from the migraine-related article with the user biometric data, and in some examples the current location of the user, to determine that providing the health-related suggestion of the article to the user may help the user quickly address and perhaps alleviate the migraine headache. In response to such correlation, the suggestion engine may transmit to the electronic personal assistant application program 24 the link 1010 to the identified article discussing possibly reducing migraine intensity with bananas. The client computing device 12 may then display the link 1010 in the GUI 510.

In some examples, a client computing device 12 such as a wearable band may control a medical device based on the health-related suggestion. In some examples the medical device 22 may comprise an electronic drug delivery device, such as a therapeutic agent dispenser. Anonymized medical record statistics 52 may comprise dosage levels prescribed by a subset of medical specialists for a particular condition. Where a user suffers from the same condition, the suggestion engine 74 may access the anonymized medical record statistics 52 to identify the most-common dosage level prescribed by the subset of medical specialists for this condition and for other persons having similar medical histories and otherwise situated similarly as the user. Using this data, the personal assistant application program 24 may control the therapeutic agent dispenser to dispense an adjusted amount of medicine to the user based on this identified dosage level.

In another example, a medical device 22 may comprise a health monitor to monitor a physiological measurement or condition, such as a blood pressure monitor. Anonymized medical record statistics 52 may be analyzed to determine average blood pressure readings for people who are being treated for various levels of hypertension. Using this data, the personal assistant application program 24 of a computing device 12 may determine one or more alert thresholds that correspond to a potential diagnosis of hypertension. The personal assistant application program 24 may then control the blood pressure monitor to activate a visual and/or audible alert when the user's blood pressure exceeds one of the alert thresholds.

Figure 11:
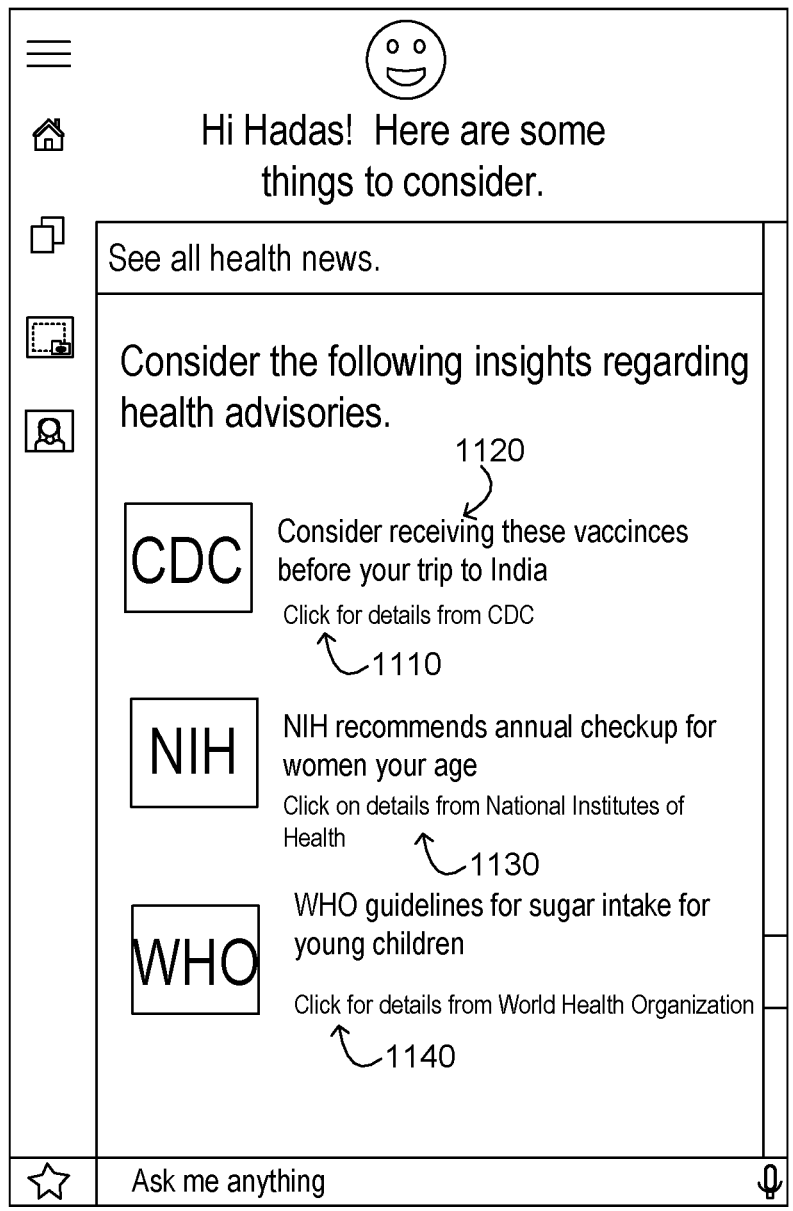
FIG. 11 is a schematic view of a display providing health-related suggestions according to other embodiments of the present description.

With reference now to FIG. 11 and in another example, the electronic personal assistant application program 24 may provide a health-related suggestion in the form of a proactive push notification of health advisories that relate the user's gender, age, race and ethnicity, place of residence of the user, geographic travel history of the user, predicted user activity of the user, such as travel, exercise workout, sporting event, etc., place of employment of the user, family unit of the user, family medical history, past medical history of the user, condition from which the user currently suffers, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, and/or health benefits information in which the user may be interested.

In some examples the suggestion engine 74 may perform searches in one or more of the user personal assistant knowledge base 30, the aggregated personal assistant knowledge base 38, the user electronic medical record 42, and the aggregated medical information knowledge base 54, subject to user authorizations via settings 44 to conduct searches using each of these databases. In one example, the personal assistant user data interpretation engine 28 may infer from calendar data that in one month the user is traveling to India for a three-month visit. The suggestion engine 74 may identify a vaccine alert for India in the alerts 60 of the aggregated medical information knowledge base 54.

A notification agent 64 within server system 14 may instruct the alert notification engine 68 of the electronic personal assistant application server 66 to send a message 70 in the form of a push notification featuring the content of the India vaccine alert 60 to the electronic personal assistant application program 24 executed on the client device 12. In one specific example, the alert may be targeted to users who the data interpretation engine 28 infers will soon travel to India, such as the user in the present example. Accordingly, the alert notification engine 68 may transmit to the electronic personal assistant application program 24 a link 1110 to the identified alert regarding India vaccines. The client computing device 12 may then display the link 1110 in the GUI 510.

In one example, personal assistant application program 24 may generate for the user and display a customized title 1120 for the alert that is based on data received from the suggestion engine 74 and/or other data from the user personal assistant knowledge base 30. In this example, the customized title 1110 makes reference to the user's upcoming trip to India, to thereby make the article more relevant to the user and increase the chances of the user clicking on the link 1110 to the alert.

In another example, the suggestion engine 74 may determine from data in the user's profile 32 that the user is a woman and is 65 years old. The suggestion engine 74 may search and locate in a third party medical information source 58 an advisory from the NIH that recommends an annual check up for women 65 years of age and older. Accordingly, the suggestion engine 74 may transmit to the electronic personal assistant application program 24 a link 1130 to the NIH advisory. The client computing device 12 may then display the link 1130 in the GUI 510.

In another example, the suggestion engine 74 may determine from data in the user's profile 32 that the user is has two children under the age of five. The suggestion engine 74 may search and locate in a third party medical information source 58 guidelines issued by the World Health Organization regarding suggested levels of sugar intake for young children. Accordingly, the suggestion engine 74 may transmit to the electronic personal assistant application program 24 a link 1140 to the WHO guidelines. The client computing device 12 may then display the link 1140 in the GUI 510.

In some examples, health-related suggestions in the form of health advisories, alerts, guidelines, etc. also may be based on anonymized statistics of a user population. For example, the suggestion engine 74 also may analyze anonymized medical record statistics 52 from the aggregated medical information knowledge base 54 to determine (or rank) those advisories, alerts, and guidelines that have been viewed most often by people who have medical conditions, health characteristics, and/or demographic data similar to a user. It will be appreciated that the foregoing examples are provided for descriptive purposes, and that many other examples using different combinations of user data 26 are possible.

In some examples, the electronic personal assistant application server 66 may determine one or more predetermined context triggers for sending a health-related suggestion to a client computing device of a user. For example, the suggestion engine 74 may comprise machine learning algorithms that, when executed, analyze user data 26 to determine one or more predetermined context triggers at which delivery of a particular health-related suggestion is more likely to result in the user consuming and/or acting on the delivered content. Upon detecting an occurrence of a predetermined context trigger, the particular health-related suggestion may be sent to the client computing device 12 of the user.

In some examples, the suggestion engine 74 may learn behaviors of the user by analyzing the user's behavior over time, including when and how the user responds to health-related suggestions. Using such user behavior information, the suggestion engine 74 may generate one or more predetermined context triggers for sending a health-related suggestion. For example, the suggestion engine 74 may learn that a user responds positively to exercise recommendations (e.g., engages in the recommended exercise) when the user receives the recommendation while the user is exercising or working out. Thus, a predetermined context trigger may be detecting that the user is exercising.

In another example, the suggestion engine 74 may learn that a different user responds positively to an exercise recommendation when it is received at least one hour before the start time of a user's workout routine (because, for example, the user likes to plan and prepare for exercise). In this example, a predetermined context trigger may comprise two hours before an exercise appointment on the user's calendar.

Figure 12A:
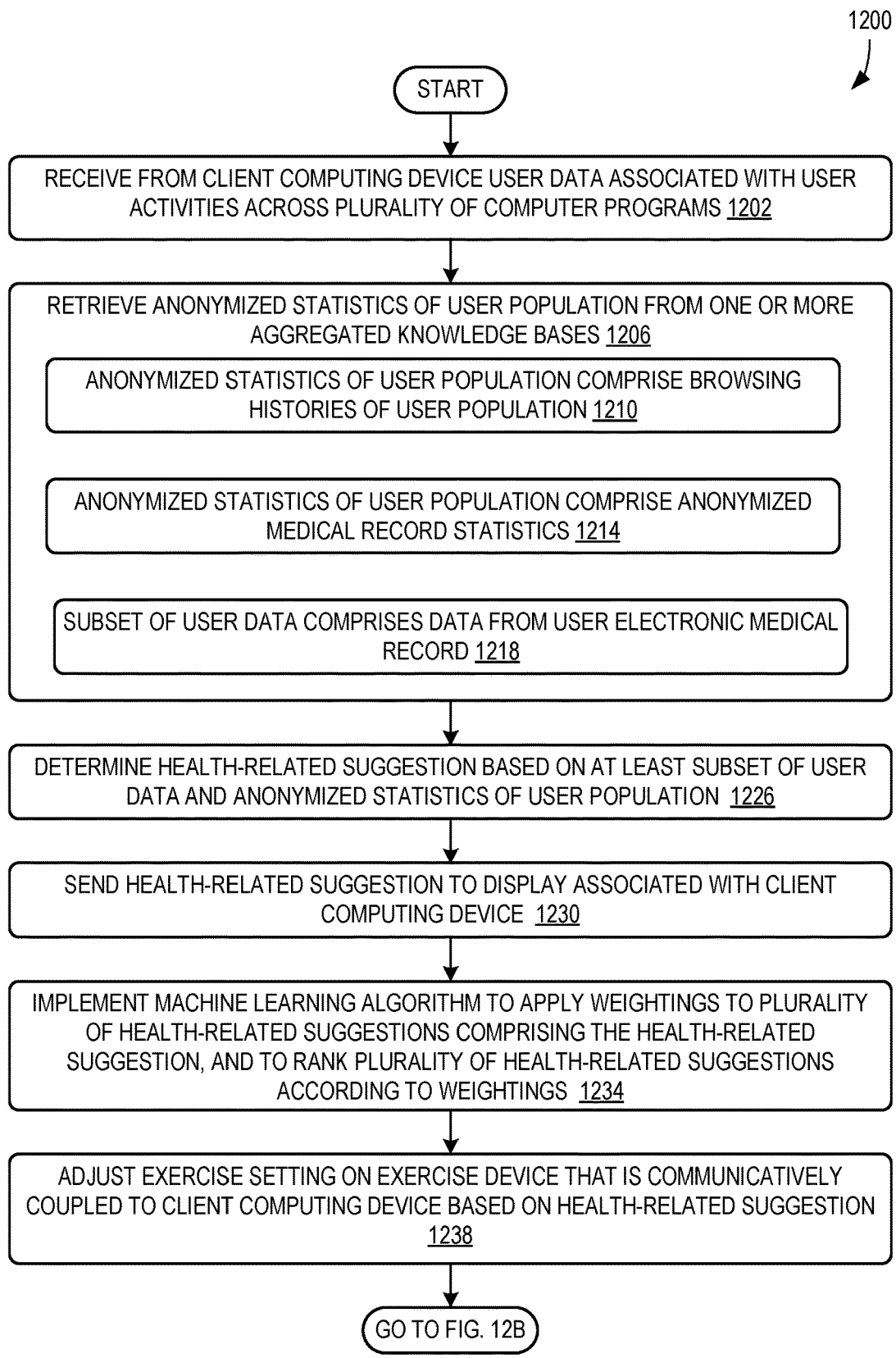
FIGS. 12A and 12B are a flow chart of a method for providing a health-related suggestion according to an embodiment of the present disclosure.
Figure 12B:
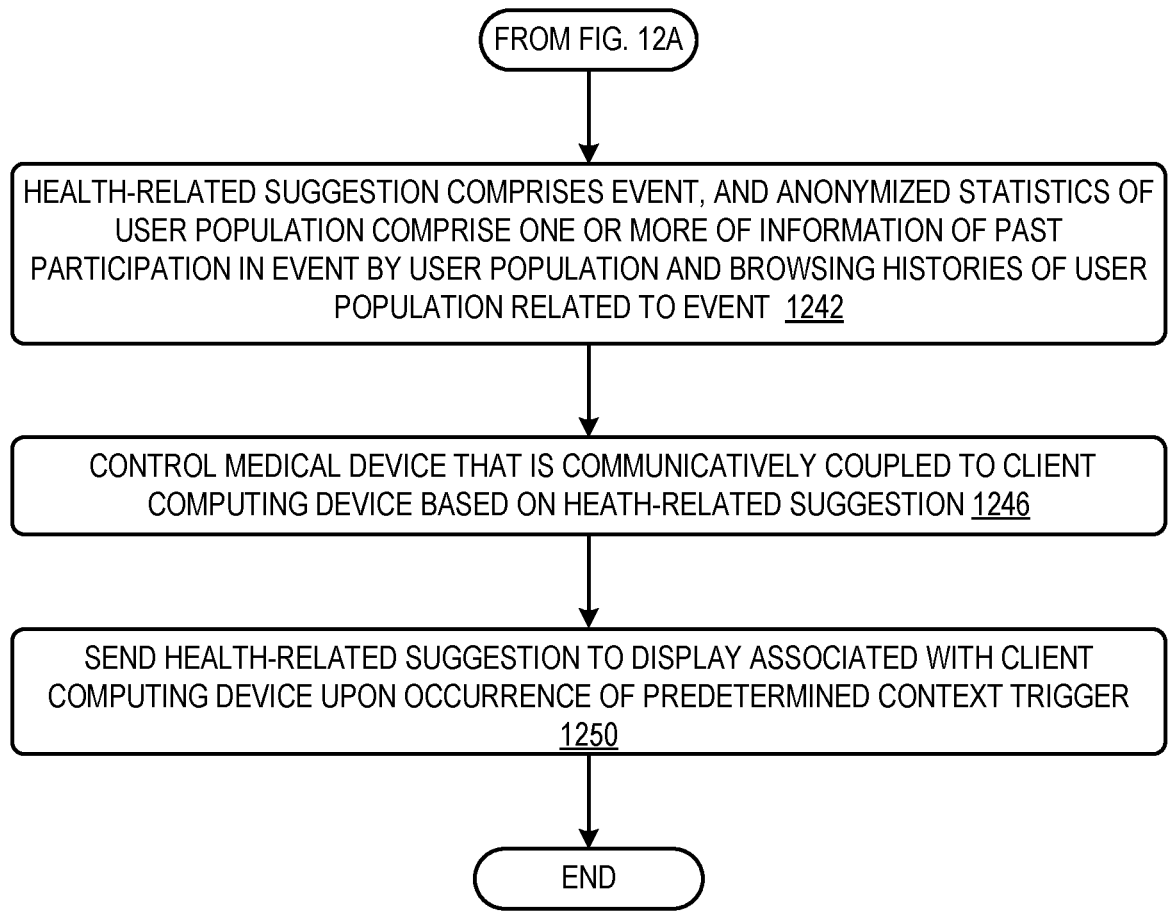

FIGS. 12A and 12B illustrate a flow chart of a method 1200 for providing a health-related suggestion according to an embodiment of the present disclosure. The following description of method 1200 is provided with reference to the software and hardware components described above and shown in FIGS. 1-10. It will be appreciated that method 1200 may also be performed in other contexts using other suitable hardware and software components.

With reference to FIG. 12A, at 1202 the method 1200 may include receiving from a client computing device user data associated with user activities across a plurality of computer programs. In one example, the user data may comprise one or more of location data, search history, download history, browse history, contacts data, social network data, and calendar data. At 1206 the method 1200 may include retrieving anonymized statistics of a user population from one or more aggregated knowledge bases. At 1210 the anonymized statistics of the user population may comprise browsing histories of the user population. At 1214 the anonymized statistics of the user population may comprise anonymized medical record statistics. At 1218 the subset of the user data may comprise data from a user electronic medical record.

At 1226 the method 1200 may include determining a health-related suggestion based on at least a subset of the user data and the anonymized statistics of a user population. At 1230 the method 1200 may include sending the health-related suggestion to a display associated with a client computing device. At 1234 the method 1200 may include implementing a machine learning algorithm to apply weightings to a plurality of health-related suggestions comprising the health-related suggestion, and to rank the plurality of health-related suggestions according to the weightings. At 1238 the method 1200 may include adjusting an exercise setting on an exercise device that is communicatively coupled to the client computing device based on the health-related suggestion.

With reference now to FIG. 12B, at 1242 the health-related suggestion may comprise an event, and the anonymized statistics of the user population may comprise one or more of information of past participation in the event by the user population and browsing histories of the user population related to the event. At 1246 the method 1200 may include controlling a medical device that is communicatively coupled to the client computing device based on the health-related suggestion. At 1250 the method 1200 may include sending the health-related suggestion upon occurrence of a predetermined context trigger.

It will be appreciated that method 1200 is provided by way of example and is not meant to be limiting. Therefore, it is to be understood that method 1200 may include additional and/or alternative steps than those illustrated in FIGS. 12A and 12B. Further, it is to be understood that method 1200 may be performed in any suitable order. Further still, it is to be understood that one or more steps may be omitted from method 1200 without departing from the scope of this disclosure.

Figure 13:
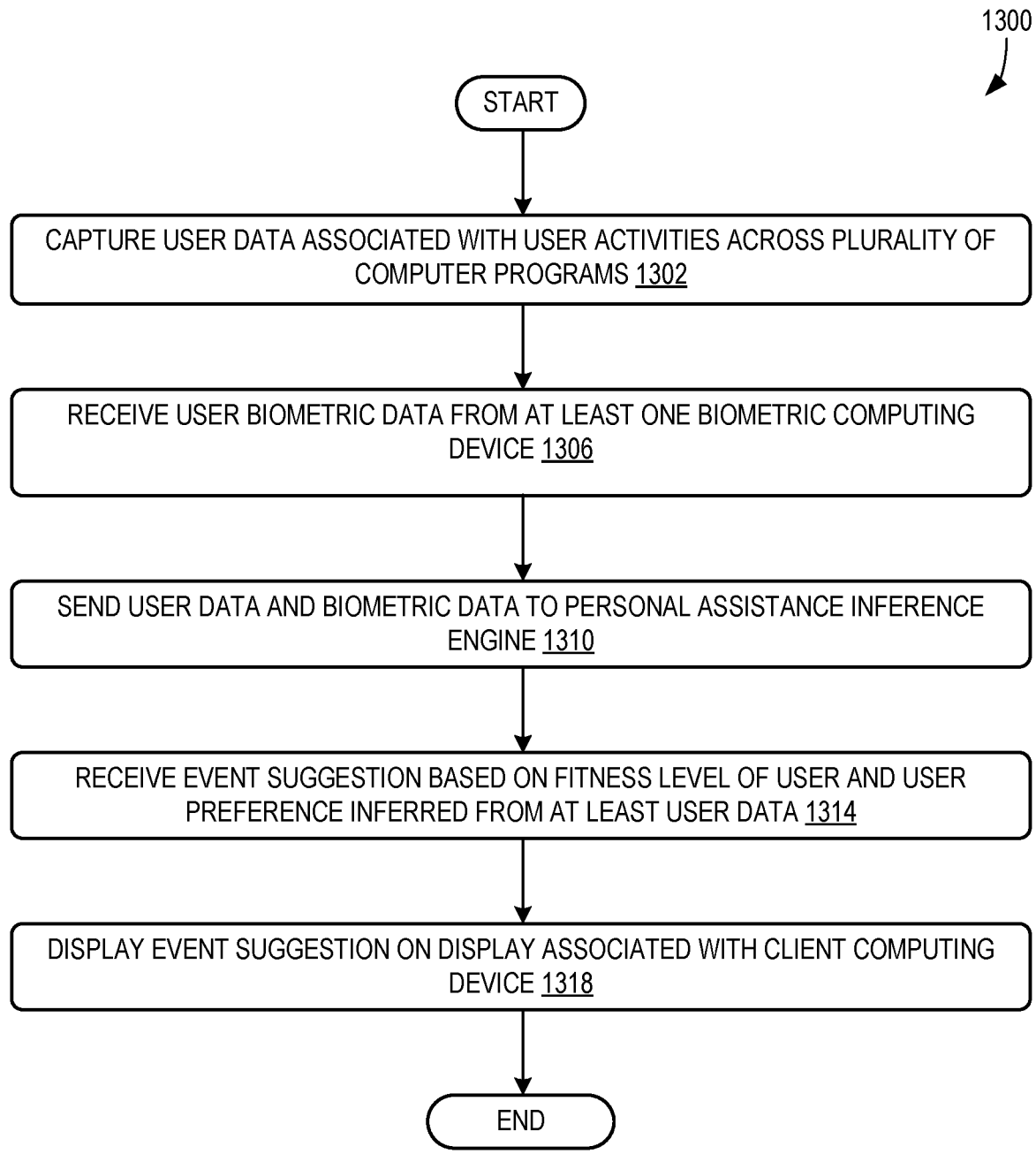
FIG. 13 is a flow chart of a method for providing a health-related suggestion according to another embodiment of the present disclosure.

FIG. 13 illustrates a flow chart of a method 1300 for providing a health-related suggestion via a client computing device according to an embodiment of the present disclosure. The following description of method 1300 is provided with reference to the software and hardware components described above and shown in FIGS. 1-10. It will be appreciated that method 1300 may also be performed in other contexts using other suitable hardware and software components.

With reference to FIG. 13, at 1302 the method 1300 may include capturing user data associated with user activities across a plurality of computer programs. At 1306 the method 1300 may include receiving user biometric data from at least one biometric computing device. At 1310 the method 1300 may include sending the user data user and the biometric data to a personal assistant user data interpretation engine. At 1314 the method 1300 may include receiving an event suggestion based on a fitness level of the user and a user preference inferred from at least the user data. At 1318 the method 1300 may include displaying the event suggestion on a display associated with the client computing device.

It will be appreciated that method 1300 is provided by way of example and is not meant to be limiting. Therefore, it is to be understood that method 1300 may include additional and/or alternative steps than those illustrated in FIG. 13. Further, it is to be understood that method 1300 may be performed in any suitable order. Further still, it is to be understood that one or more steps may be omitted from method 1300 without departing from the scope of this disclosure.

In some embodiments, the methods and processes described herein may be tied to a computing system of one or more computing devices. In particular, such methods and processes may be implemented as a computer-application program or service, an application-programming interface (API), a library, and/or other computer-program product.

Figure 14:
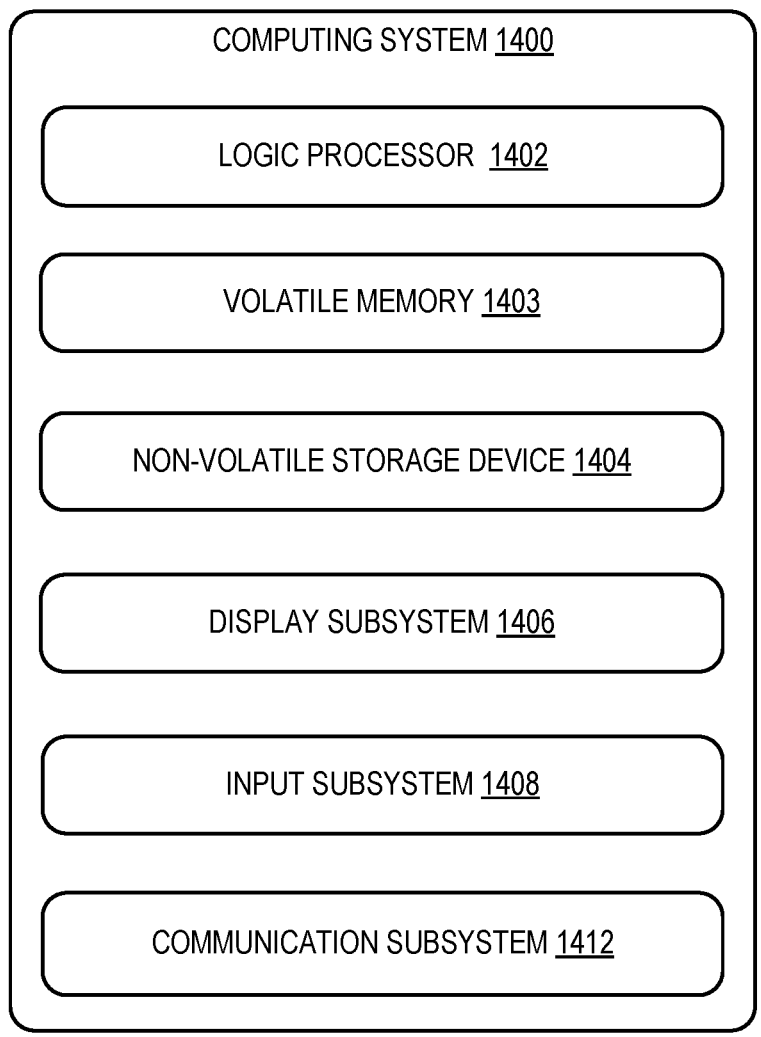
FIG. 14 is simplified schematic illustration of an embodiment of a computing device.

FIG. 14 schematically shows a non-limiting embodiment of a computing system 1400 that can enact one or more of the methods and processes described above. Computing system 1400 is shown in simplified form. Computing system 1400 may embody one or more of the servers or client computing devices 12 or other computing devices 16 of FIG. 1. Computing system 1400 may take the form of one or more personal computers, server computers, tablet computers, home-entertainment computers, network computing devices, gaming devices, mobile computing devices, mobile communication devices (e.g., smart phone), and/or other computing devices, wearable computing devices such as smart wristwatches and head mounted augmented reality devices, computerized medical devices.

Computing system 1400 includes a logic processor 1402 volatile memory 1403, and a non-volatile storage device 1404. Computing system 1400 may optionally include a display subsystem 1406, input subsystem 1408, communication subsystem 1412, and/or other components not shown in FIG. 14.

Logic processor 1402 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 1402 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 1404 includes one or more physical devices configured to hold instructions executable by the logic processors to implement the methods and processes described herein. When such methods and processes are implemented, the state of non-volatile storage device 94 may be transformed—e.g., to hold different data.

Non-volatile storage device 1404 may include physical devices that are removable and/or built-in. Non-volatile storage device 94 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 1404 may include nonvolatile, dynamic, static, read/write, read-only, sequential-access, location-addressable, file-addressable, and/or content-addressable devices. It will be appreciated that non-volatile storage device 1404 is configured to hold instructions even when power is cut to the non-volatile storage device 1404.

Volatile memory 1403 may include physical devices that include random access memory. Volatile memory 1403 is typically utilized by logic processor 1402 to temporarily store information during processing of software instructions. It will be appreciated that volatile memory 1403 typically does not continue to store instructions when power is cut to the volatile memory 1403.

Aspects of logic processor 1402, volatile memory 1403, and non-volatile storage device 1404 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1400 typically implemented in software by a processor to perform a particular function using portions of volatile memory, which function involves transformative processing that specially configures the processor to perform the function. Thus, a module, program, or engine may be instantiated via logic processor 1402 executing instructions held by non-volatile storage device 1404, using portions of volatile memory 1403. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 1406 may be used to present a visual representation of data held by non-volatile storage device 1404. Display subsystem 1406 may include a non-see-through display and/or an at least partially see through display. The visual representation may take the form of a graphical user interface (GUI). As the herein described methods and processes change the data held by the non-volatile storage device, and thus transform the state of the non-volatile storage device, the state of display subsystem 1406 may likewise be transformed to visually represent changes in the underlying data. Display subsystem 1406 may include one or more display devices utilizing virtually any type of technology. Such display devices may be combined with logic processor 1402, volatile memory 1403, and/or non-volatile storage device 1404 in a shared enclosure, or such display devices may be peripheral display devices.

When included, input subsystem 1408 may comprise or interface with one or more user-input devices such as a keyboard, mouse, touch screen, or game controller. In some embodiments, the input subsystem may comprise or interface with selected natural user input (NUT) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 1412 may be configured to communicatively couple various computing devices described herein with each other, and with other devices. Communication subsystem 1412 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 1400 to send and/or receive messages to and/or from other devices via a network such as the Internet.

The present disclosure includes the following additional aspects. One aspect provides a client computing device for providing a health-related suggestion, comprising: a processor and an electronic personal assistant application program executable by the processor, with the personal assistant application program configured to: capture user data associated with user activities across a plurality of computer programs; send the user data to a personal assistant user data interpretation engine; receive a health-related suggestion based on at least a subset of the user data and anonymized statistics of a user population retrieved from an aggregated knowledge base; and display the health-related suggestion on a display associated with the client computing device. The client computing device may additionally or optionally include, wherein the personal assistant application program is further configured to adjust an exercise setting on an exercise device that is communicatively coupled to the client computing device based on the health-related suggestion. The client computing device may additionally or optionally include, wherein the personal assistant application program is further configured to control a medical device that is communicatively coupled to the client computing device based on the health-related suggestion. The client computing device may additionally or optionally include, wherein the anonymized statistics of the user population are processed by a machine learning algorithm to apply weightings and rank a plurality of health-related suggestions comprising the health-related suggestion. The client computing device may additionally or optionally include, wherein the anonymized statistics of the user population comprise browsing histories of the user population. The client computing device may additionally or optionally include, wherein the anonymized statistics of the user population comprise anonymized medical record statistics. The client computing device may additionally or optionally include, wherein the anonymized statistics of the user population are based on a predefined cohort of the user population. The client computing device may additionally or optionally include, wherein the subset of the user data comprises data from a user electronic medical record. The client computing device may additionally or optionally include, wherein the subset of the user data comprises data from a browsing history of a user. The client computing device may additionally or optionally include, wherein the personal assistant application program is further configured to: receive user biometric data from at least one biometric computing device; and send the user biometric data to the personal assistant user data interpretation engine, wherein the subset of the user data comprises the user biometric data.

Another aspect provides a method for providing a health-related suggestion, comprising: receiving from a client computing device user data associated with user activities across a plurality of computer programs; retrieving anonymized statistics of a user population from one or more aggregated knowledge bases; determining a health-related suggestion based on at least a subset of the user data and the anonymized statistics of a user population; and sending the health-related suggestion to a display associated with a client computing device. The method may additionally or optionally include adjusting an exercise setting on an exercise device that is communicatively coupled to the client computing device based on the health-related suggestion. The method may additionally or optionally include controlling a medical device that is communicatively coupled to the client computing device based on the health-related suggestion. The method may additionally or optionally include implementing a machine learning algorithm to apply weightings to a plurality of health-related suggestions comprising the health-related suggestion, and to rank the plurality of health-related suggestions according to the weightings. The method may additionally or optionally include, wherein the anonymized statistics of the user population comprise browsing histories of the user population. The method may additionally or optionally include, wherein the anonymized statistics of the user population comprise anonymized medical record statistics. The method may additionally or optionally include, wherein the subset of the user data comprises data from a user electronic medical record. The method may additionally or optionally include, wherein sending the health-related suggestion to a display associated with a client computing device further comprises sending the health-related suggestion upon occurrence of a predetermined context trigger. The method may additionally or optionally include, wherein the health-related suggestion comprises an event, and the anonymized statistics of the user population comprise one or more of information of past participation in the event by the user population and browsing histories of the user population related to the event.

Another aspect provides a client computing device for providing a health-related suggestion, comprising: a processor and an electronic personal assistant application program executable by the processor, the personal assistant application program configured to: capture user data associated with user activities across a plurality of computer programs; send the user data to a personal assistant user data interpretation engine; receive a health-related suggestion based on at least a subset of the user data and anonymized statistics of a user population, wherein the anonymized statistics of the user population are processed by a machine learning algorithm to apply weightings and rank a plurality of health-related suggestions comprising the health-related suggestion; and display the health-related suggestion on a display associated with the client computing device.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A client computing device for providing a health-related suggestion, comprising:
    a processor; and
    an electronic personal assistant application program executable by the processor, the personal assistant application program configured to:
        capture user data associated with user activities of a user across a plurality of computer programs;
        send the user data to a personal assistant user data interpretation engine to determine one or more predetermined context triggers for delivery of the health-related suggestion to the client computing device of the user by application of a machine learning algorithm to the user data;
        receive, from a remote computing device over a communications network, the health-related suggestion that is based on at least a subset of the user data and anonymized statistics of a user population retrieved from an aggregated knowledge base, wherein delivery of the health-related suggestion by the remote computing device is triggered by detection of an occurrence of a predetermined context trigger of the one or more predetermined context triggers;
        based on the health-related suggestion, generate instructions for controlling an electronic drug delivery device to dispense an adjusted amount of a therapeutic agent, wherein the processor determines the adjusted amount of the therapeutic agent based at least on the anonymized statistics of the user population retrieved from the aggregated knowledge base; and
        transmit the instructions to the electronic drug delivery device to dispense the adjusted amount of the therapeutic agent.

2. The client computing device of claim 1, wherein the personal assistant application program is further configured to adjust an exercise setting on an exercise device that is communicatively coupled to the client computing device based on the health-related suggestion.

3. The client computing device of claim 1, wherein the personal assistant application program is further configured to control another medical device that is communicatively coupled to the client computing device based on the health-related suggestion.

4. The client computing device of claim 1, wherein the anonymized statistics of the user population are processed by the machine learning algorithm to apply weightings and rank a plurality of health-related suggestions comprising the health-related suggestion.

5. The client computing device of claim 1, wherein the anonymized statistics of the user population comprise browsing histories of the user population.

6. The client computing device of claim 1, wherein the anonymized statistics of the user population comprise anonymized medical record statistics.

7. The client computing device of claim 1, wherein the anonymized statistics of the user population are based on a predefined cohort of the user population.

8. The client computing device of claim 1, wherein the subset of the user data comprises data from a user electronic medical record.

9. The client computing device of claim 1, wherein the subset of the user data comprises data from a browsing history of the user.

10. The client computing device of claim 1, wherein the personal assistant application program is further configured to:
    receive user biometric data from at least one biometric computing device; and
    send the user biometric data to the personal assistant user data interpretation engine,
    wherein the subset of the user data comprises the user biometric data.

11. A method enacted at a remote computing device for providing a health-related suggestion, comprising:
    receiving from a client computing device over a communications network user data associated with user activities of a user across a plurality of computer programs;
    retrieving anonymized statistics of a user population from one or more aggregated knowledge bases;
    determining the health-related suggestion based on at least a subset of the user data and the anonymized statistics of the user population;
    using a machine learning algorithm to determine a predetermined context trigger associated with the user of the client computing device for delivery of the health-related suggestion to the client computing device of the user; and
    upon detection of an occurrence of the predetermined context trigger, sending the health-related suggestion to the client computing device, thereby causing the client computing device to:
        based on the health-related suggestion, generate instructions for controlling an electronic drug delivery device to dispense an adjusted amount of a therapeutic agent, wherein the adjusted amount of the therapeutic agent is determined based at least on the anonymized statistics of the user population retrieved from the aggregated knowledge base, and
        transmit the instructions to the electronic drug delivery device to dispense the adjusted amount of the therapeutic agent.

12. The method of claim 11, further comprising adjusting an exercise setting on an exercise device that is communicatively coupled to the client computing device based on the health-related suggestion.

13. The method of claim 11, further comprising controlling another medical device that is communicatively coupled to the client computing device based on the health-related suggestion.

14. The method of claim 11, further comprising implementing the machine learning algorithm to apply weightings to a plurality of health-related suggestions comprising the health-related suggestion, and to rank the plurality of health-related suggestions according to the weightings.

15. The method of claim 11, wherein the anonymized statistics of the user population comprise browsing histories of the user population.

16. The method of claim 11, wherein the anonymized statistics of the user population comprise anonymized medical record statistics.

17. The method of claim 11, wherein the subset of the user data comprises data from a user electronic medical record.

18. The method of claim 11, wherein the health-related suggestion comprises an event, and the anonymized statistics of the user population comprise one or more of information of past participation in the event by the user population and browsing histories of the user population related to the event.

19. A client computing device for providing a health-related suggestion, comprising:
- a processor; and
- an electronic personal assistant application program executable by the processor, the personal assistant application program configured to:
  - capture user data associated with user activities of a user across a plurality of computer programs;
  - send the user data to a personal assistant user data interpretation engine to determine one or more predetermined context triggers for delivery of the health-related suggestion to the client computing device of the user by application of a machine learning algorithm to the user data;
  - receive, from a remote computing device over a communications network, the health-related suggestion that is based on at least a subset of the user data and anonymized statistics of a user population retrieved from an aggregated knowledge base, wherein the anonymized statistics of the user population are processed by the machine learning algorithm to apply weightings and rank a plurality of health-related suggestions comprising the health-related suggestion, wherein delivery of the health-related suggestion by the remote computing device is triggered by detection of an occurrence of a predetermined context trigger of the one or more predetermined context triggers;
- based on the health-related suggestion, generate instructions for controlling an electronic drug delivery device to dispense an adjusted amount of a therapeutic agent, wherein the processor determines the adjusted amount of the therapeutic agent based at least on the anonymized statistics of the user population retrieved from the aggregated knowledge base; and
- transmit the instructions to the electronic drug delivery device to dispense the adjusted amount of the therapeutic agent.

* * * * *